US008846725B2

(12) United States Patent
Johnson et al.

(10) Patent No.: US 8,846,725 B2
(45) Date of Patent: Sep. 30, 2014

(54) HIGHLY PENETRATING COMPOSITIONS AND METHODS FOR TREATING PATHOGEN-INDUCED DISORDERED TISSUES

(75) Inventors: B. Ron Johnson, Sandy, UT (US); James P. McCarthy, Sandy, UT (US)

(73) Assignee: Quadex Pharmaceuticals, LLC, Midvale, UT (US)

( * ) Notice: Subject to any disclaimer, the term of this patent is extended or adjusted under 35 U.S.C. 154(b) by 492 days.

(21) Appl. No.: 13/012,719

(22) Filed: Jan. 24, 2011

(65) Prior Publication Data

US 2012/0190715 A1    Jul. 26, 2012

(51) Int. Cl.
*A61K 31/14*     (2006.01)
*A61K 31/245*    (2006.01)
*A61K 47/10*     (2006.01)
*A61K 45/06*     (2006.01)
*A61K 31/4425*   (2006.01)
*A61K 31/155*    (2006.01)
*A61K 9/08*      (2006.01)
*A61K 9/00*      (2006.01)

(52) U.S. Cl.
CPC . *A61K 9/08* (2013.01); *A61K 45/06* (2013.01); *A61K 31/4425* (2013.01); *A61K 31/155* (2013.01); *A61K 31/245* (2013.01); *A61K 31/14* (2013.01); *A61K 9/0014* (2013.01); *A61K 47/10* (2013.01)
USPC ............................ 514/358; 514/536; 514/643

(58) Field of Classification Search
None
See application file for complete search history.

(56) References Cited

U.S. PATENT DOCUMENTS

| | | |
|---|---|---|
| 1,519,693 A | 12/1924 | Moore |
| 3,832,460 A | 8/1974 | Kosti |
| 4,176,197 A | 11/1979 | Olson |
| 4,199,574 A | 4/1980 | Schaeffer |
| 4,262,007 A | 4/1981 | Sherrill |
| 4,390,539 A | 6/1983 | Sherrill |
| 4,556,557 A | 12/1985 | Reichert |
| 4,874,794 A | 10/1989 | Katz |
| 4,952,204 A | 8/1990 | Korteweg |
| 4,979,420 A | 12/1990 | Cusack |
| 5,403,864 A | 4/1995 | Bruch et al. |
| 5,492,932 A | 2/1996 | Kundsin |
| 5,540,934 A | 7/1996 | Touitou |
| 5,631,245 A | 5/1997 | Drube |
| 5,704,906 A | 1/1998 | Fox |
| 5,753,270 A | 5/1998 | Beauchamp |
| 5,767,163 A | 6/1998 | Kundsin |
| 6,211,243 B1 | 4/2001 | Johnson |
| 6,355,684 B1 | 3/2002 | Squires |
| 6,410,599 B1 | 6/2002 | Johnson |
| 6,414,032 B1 | 7/2002 | Johnson |
| 6,420,431 B1 | 7/2002 | Johnson |
| 6,423,750 B1 | 7/2002 | Johnson |
| 6,759,434 B2 | 7/2004 | Johnson |
| 2004/0186183 A1 | 9/2004 | Johnson |
| 2006/0135464 A1 | 6/2006 | Johnson |

FOREIGN PATENT DOCUMENTS

| | | |
|---|---|---|
| CA | 2259709 | 7/1999 |
| DE | 4328828 | 3/1995 |
| DE | 69624340 | 6/2003 |
| EP | 0175338 | 3/1986 |
| EP | 0190797 | 8/1986 |
| EP | 0308210 | 3/1989 |
| EP | 0357261 | 3/1990 |
| EP | 0487066 | 5/1992 |
| EP | 0872248 | 10/1998 |
| EP | 0937394 | 8/1999 |
| EP | 1023899 | 8/2000 |
| GB | 1574302 | 9/1980 |
| JP | 61-76401 | 6/1994 |
| JP | 8-164191 | 6/1996 |
| JP | 8-217694 | 8/1996 |
| JP | 10-324624 | 12/1998 |
| WO | WO 95/03734 | 2/1995 |
| WO | WO 97/29742 | 8/1997 |
| WO | WO 98/11778 | 3/1998 |
| WO | WO 99/12545 | 3/1999 |
| WO | WO 99/16447 | 8/1999 |

OTHER PUBLICATIONS

Zatz, L. J. Modification of Skin Permeatation by Solvents, Cosmetics and Toiletries vol. 106, Feb. 1991, p. 91-98.
Zatz, L. J. "Enhancing Skin Penetration of Actives with the Vehicle", Cosmetics and Toiletries, vol. 109, Sep. 1994, p. 27-36.
Kunta, J. R. et al., "Effect of mentol and related terpenes on the percutaneous absorption of propanol across excised hairless mouse skin", Jounal of Paharmaceutical Science vol. 86, No. 12, pp. 1369-1373, Dec. 1997.
Encylopedia of Chemistry, vol. 1, ed. Editorial committee for Encyclopedia of Chemistry, Kyoritsu Shuppan Co. Ltd, Feb. 15, 1987, p. 888.
U.S. Appl. No. 09/401,076, Aug. 3, 2000, Office Action.
U.S. Appl. No. 09/401,076, Nov. 1, 2000, Notice of Allowance.
U.S. Appl. No. 09/993,178, Jan. 15, 2002, Office Action.
U.S. Appl. No. 09/993,178, Mar. 26, 2002, Notice of Allowance.
U.S. Appl. No. 09/668,953, Sep. 25, 2001, Office Action.
U.S. Appl. No. 09/668,953, Mar. 4, 2002, Notice of Allowance.
U.S. Appl. No. 10/200,897, Aug. 20, 2003, Office Action.

(Continued)

Primary Examiner — Anna Pagonakis
(74) Attorney, Agent, or Firm — Workman Nydegger

(57) ABSTRACT

Compositions and methods for treating disordered tissues, such as caused by pathogens and/or by toxins. The treatment compositions include an anti-infective active agent, a liquid carrier, and benzocaine in an amount so that the treatment composition penetrates more quickly into disordered tissue compared to the treatment composition in the absence of the benzocaine. In addition, the benzocaine can increase residence time of the anti-infective active in the treatment area. The preferred anti-infective active agent can be an organohalide, such as a quaternary ammonium halide compound, an example of which is benzalkonium chloride. The treatment compositions and methods may employ the use of an applicator adapted for use in promoting penetration of the treatment composition and/or agitation of the disordered tissue to further enhance penetration.

18 Claims, 9 Drawing Sheets

(56) References Cited

OTHER PUBLICATIONS

U.S. Appl. No. 10/200,897, Jan. 16, 2004, Notice of Allowance.
U.S. Appl. No. 10/816,571, Nov. 28, 2007, Office Action.
U.S. Appl. No. 10/816,571, May 22, 2008, Office Action.
U.S. Appl. No. 10/816,571, Sep. 17, 2009, Office Action.
U.S. Appl. No. 10/816,571, Mar. 30, 2010, Office Action.
U.S. Appl. No. 10/816,571, Dec. 21, 2010, Office Action.
U.S. Appl. No. 11/348,127, Oct. 4, 2007, Office Action.
U.S. Appl. No. 11/348,127, Feb. 29, 2008, Office Action.
U.S. Appl. No. 09/668,951, Sep. 21, 2001, Office Action.
U.S. Appl. No. 09/668,951, Feb. 26, 2002, Notice of Allowance.
U.S. Appl. No. 09/669,068, Sep. 27, 2001, Office Action.
U.S. Appl. No. 09/669,068, Feb. 26, 2002, Notice of Allowance.
U.S. Appl. No. 09/668,949, Sep. 13, 2001, Office Action.
U.S. Appl. No. 09/669,067, Sep. 25, 2001, Office Action.
U.S. Appl. No. 09/668,950, Sep. 13, 2001, Office Action.
Declaration of B. Ron Johnson dated Sep. 16, 2011 and Supporting Exhibits.
J.S. Armstrong and E.J. Froelich—Inactivation of Viruses by Benzalkonium Chloricle—Applied Microbiology, Mar. 1964, vol. 12, No. 2, p. 132-137.

HIGHLY PENETRATING COMPOSITIONS AND METHODS FOR TREATING PATHOGEN-INDUCED DISORDERED TISSUES

BACKGROUND OF THE INVENTION

1. The Field of the Invention

The invention relates to treatment compositions and methods for treatment of disordered tissues, such as those caused by a virus, fungus, or bacteria.

2. The Relevant Technology

Tissue disorders caused by pathogens, particularly those which impact epithelial tissue and are caused by the Herpes virus, such as Herpes Simplex Types I and II and Herpes Zoster (shingles), cold sores, genital herpes, or, *candida albicans*, chicken pox, acne, psoriasis, eczema, seborrhea, and dermatitis, are common but often difficult to treat. Herpes simplex virus (HSV-I and HSV-II) and Herpes Varicella-Zoster (chicken pox, shingles), commonly referred to as herpes virus or herpes, is an infectious disease which has reached crisis proportions nationally with estimated numbers of infected people at 70%-80% of U.S. population as reported by the American Social Health Association (ASHA). Other literature sources put the number of infected Americans at 85%-90% of the adult population.

Herpes virus enters the human body through minuscule breaks in the epidermal tissue, usually by contact with an infected host, and is marked by eruption of one or more vesicles, usually in groups, following an incubation period of approximately two to ten days. Typically, the course of the infectious outbreak initiates with the prodromal stage, advancing to vesicular eruption, followed by ulceration, coalescing, resolution by formation of scab, and the latency period. The outbreak can last for several weeks and, on average, lasts one to three weeks. In some immune compromised individuals, the outbreak can last for months. The vesicles can appear anywhere on epithelial tissues including the skin or mucosa, typically appearing on the lips as cold sores, glands, and oral mucosa. More severe cases may involve the conjunctiva and cornea. Genital herpes may involve the genitalia, anal mucosa and peri-anal tissue.

Herpes symptoms include inguinal swelling, pain, fever, malaise, headaches, muscle aches, and swollen glands. During latency, the virus lies dormant in the trigeminal nerve ganglia. Some individuals with oral herpes have excruciating facial pain, difficulty swallowing, eating and facial swelling. Individuals with the herpes that impacts the sacral nerve (genital herpes) have pain in the genital area, upper leg pain, swelling, and on occasion great difficulty walking.

Herpes simplex virus (HSV) infection, whether oral or genital, is recurring, residing in the nerve ganglia, then recurring due to some, as yet unknown, mechanism. Recurrent herpetic infections can be precipitated by numerous stimuli, including exposure to sunlight, nutritional deficiencies, stress, menstruation, immunosuppression, certain foods, drugs, and febrile illness.

Herpes infections can pose serious health threats, often causing blindness if the virus infects the cornea, increased cancer risk of the cervix, aseptic meningitis and encephalitis, neonatal deaths, viremia, the spread of the human immunodeficiency virus (HIV), etc. The devastating effects of this disease go well beyond the medical scope of human suffering. HSV can be responsible for serious psychological and emotional distress as well as substantial economic loss. Individuals with Auto Immune Deficiency Syndrome (AIDS) are seriously immune-compromised and can suffer especially debilitating outbreaks of HSV.

Various treatments for herpes have been proposed and include topical application of such agents as povidone-iodine, idoxuridine, trifluorothyidine, or acyclovir and its analogs. Such treatments have met with varying degrees of success. Most treatments have proven disappointing. Acyclovir and similar analogs, acyclic nucleosides, are taken orally for systemic treatment of HSV or they are applied topically. Acyclovir is somewhat effective in inhibiting the activity of several herpes viruses. However, acyclovir is only successful in interrupting the replication of the virus and is used to treat infectious outbreak systemically. Denavir is the topical version of an acyclovir analog. Few topical treatments have proven to be effective and all nucleoside treatments must be applied at first signs and symptoms of disease to achieve maximum effectiveness.

Biologically active antiviral and antimicrobial compositions have been met with marginal success when administered topically for tissue disorders. Such compositions have been applied as gels, creams, lotions, oils, ointments, pastes, tinctures, emulsions, and colloidal suspensions. Most of the compositions are oil-based to ensure the composition has sufficient viscosity and/or tackiness to remain on the surface of the skin without being rubbed off. In fact, such compositions are often absorbed into clothing more than into the skin due to a relatively slow epidermal penetration rate. Even when sufficient time is allowed for the compositions to penetrate, they are often not sufficiently effective in treating the disordered tissue and must generally be applied repeatedly over a period of days or even weeks.

Many efforts have been undertaken to remedy the inadequacies of topically administered compositions. The therapeutic effects of such compositions depend upon the specific active agent and the method of application. Many compositions contain ingredients that may provide symptomatic relief of pain and itching but are not claimed to be effective against Herpes infection except drugs based on acyclovir technology, which are purported to have some topical efficacy. Most compositions intended to treat such disorders do not effectively treat the discomfort and the disease symptoms, let alone cure the disorder or put it into a significant remission.

One useful treatment composition, sold under the name Viroxyn®, has been effective in providing relief for cold sores. Viroxyn® is covered by one or more of the following U.S. Pat. Nos. 6,759,434; 6,423,750; 6,420,431; 6,414,032; 6,410,599; and 6,211,243, the disclosures of which are incorporated herein by reference. When used as instructed, which includes using a specifically designed applicator to vigorously rub or burnish the composition into the cold sore, Viroxyn can be effective in reducing the healing time of a cold sore. Vigorous rubbing is required to force the composition to penetrate into the cold sore to a depth sufficient to kill the viruses causing the infection.

An example of a less useful composition and treatment method is provided in U.S. Pat. No. 5,753,270 to Beauchamp et al. This patent discloses a composition that includes: (a) an antiseptic and/or anesthetic compound which is (i) a terpene, such as menthol or eucalyptol or (ii) a phenolic compound, such as thymol; (b) a quaternary ammonium antiseptic compound, such as benzethonium chloride; and (c) an antiseptic compound containing iodine, salts thereof and/or complexes thereof dissolved in an organic solvent, such as a mixture of water and acetone. The composition requires application to the afflicted area in a sequence that includes 3 to 4 applications over a one minute period, which is then repeated every 3 minutes over a 10 minute period. The entire procedure is then repeated every ½ to 1 hour for 2 to 3 hours or until activity is stopped and healing is evident. The composition must therefore be applied many times over an extended period of time to be effective, which greatly diminishes compliance and effectiveness.

SUMMARY OF DISCLOSED EMBODIMENTS

The disclosure relates to the treatment of disordered tissues caused by pathogens (e.g., viruses, bacteria or fungi). An applicator may be used to apply a treatment composition comprising an anti-infective active agent in a carrier. The method includes applying the treatment composition to the disordered tissue treatment site with the applicator under conditions that enable the active agent to rapidly penetrate the disordered tissue. Gentle rubbing may assist penetration but may not be required in all cases due to enhanced penetration of the treatment composition.

An important issue when applying the treatment composition to a painful cold sore or other disordered tissue is proper compliance by the user. Solvent carriers, such as isopropyl alcohol, ethanol, acetone, and the like, can cause excruciating pain when applied to sensitive disordered tissues such as cold sores, genital herpes, and shingles. Such pain can discourage compliance by the user and undermine the effectiveness of an otherwise effective treatment composition.

It has now been discovered that adding benzocaine in specific amounts to a treatment composition that includes an organic solvent carrier, such as isopropyl alcohol, greatly increases the effectiveness in treating disordered tissues. Unexpectedly, benzocaine, when included in specific amounts, can increase the ability of such treatment compositions to penetrate into the disordered tissue in order for the active agent to more quickly contact and kill viruses or other pathogens within the disordered tissue. In addition, benzocaine also enhances efficacy by increasing kill time by at least 10% and typically by about 20-100%. It does this blocking influx of interstitial fluid into the disordered tissue, which helps to retain the active agent in the treatment area rather than being displaced by interstitial fluid. Benzocaine can also increase patient compliance by reducing the pain associated with application of the anti-infective composition to painful disordered tissue, particularly with open sores. However, beyond merely reducing pain, benzocaine has been found to increase efficacy of treatment because it promotes faster penetration of the treatment composition into disordered tissue, which reduces the amount of rubbing or agitation that would otherwise be required for the composition to be effective. It also increases residence time of the active agent in the treatment site.

The amount of benzocaine within the treatment composition must be high enough to enhance penetration, and preferably increase kill time and help alleviate pain. However, the amount of benzocaine is advantageously not so high as to leave a residue on the surface of the skin and/or cause loss of sensation in surrounding tissue and/or for a prolonged period of time (e.g., greater than about 15 minutes). For example, if included in excessive amounts, benzocaine can cause numbing of a substantial portion of a person's lips for an extended period of time, which can inhibit normal activities such as drinking and talking (e.g., as can occur after a person leaves a dental office after receiving an injection of novocaine).

The amount of benzocaine is most effective when numbing is temporary and goes away once the treatment composition has effectively penetrated into the disordered tissue and resided long enough in the disordered tissue to kill the pathogens and neutralize inflammatory agents in the tissue causing the pain. According to one embodiment, the amount of benzocaine is selected to provide a numbing effect for a time period of about 1 minute to about 20 minutes, preferably about 2 minutes to about 15 minutes, more preferably about 3 minutes to about 10 minutes, and most preferably about 4 minutes to about 8 minutes after numbing first occurs. It is desirable to include an amount of benzocaine so that numbing begins in about 10 seconds or less after application of the treatment composition, preferably in about 8 seconds or less, more preferable in about 6 seconds or less, and most preferably in about 4 seconds or less.

The highly penetrating compositions are formulated, as a result of including benzocaine in combination with a penetrating carrier, so as to penetrate quickly so that the treatment composition is no longer detected on the skin surface after less than about 1 minute, preferably less than about 40 seconds, more preferably less than about 20 seconds, and most preferably less than about 10 seconds. Pathogens are killed and inflammatory agents are destroyed within minutes or seconds after effective penetration such that it is desirable for the numbing effect of benzocaine to subside within about 10 minutes of application, preferably within about 8 minutes, more preferably within about 6 minutes, and most preferably within about 5 minutes.

After extensive comparative survey testing supervised by learned health care intermediates (i.e., doctors and dentists), which included obtaining feedback from patients (to whom the benzocaine-containing treatment compositions were administered by the learned health care intermediates), who in this case suffered from painful and highly infective cold sores, it was determined that the most effective amount of benzocaine within treatment compositions that also included a liquid carrier comprised of 70% by volume isopropyl alcohol in water and 0.13% by weight benzalkonium chloride was between about 2.5% and about 7.5% by weight. Above 7.5%, a benzocaine residue was sometimes detected. Below about 2%, benzocaine did not significantly enhance penetration. Between about 2.5% to about 7.5%, however, benzocaine enhanced penetration, increased kill time, and caused temporary, but not excessive, numbing when using the treatment compositions that were tested. A more optimal range for this anti-infective composition is about 2.75% to about 6% benzocaine by weight, and the most optimal range was found to be about 3% to about 5% benzocaine by weight.

Nevertheless, depending on the type of carrier that is used, particularly if it is less penetrating than a mixture of about 70% by volume isopropyl alcohol and 30% water (e.g., about 10-50%, or about 15-40%, or about 20-30% by volume isopropyl alcohol with the balance comprising mostly water), the amount of benzocaine can be increased in order to promote enhanced penetration and enhance kill time, and can be as high as 20% by weight, although this amount may cause prolonged numbing (e.g., 1-3 hours). When using a liquid carrier that is significantly less penetrating than a 70/30 v/v mixture of isopropyl alcohol and water, the amount of benzocaine can be included in a range of about 3.5% to about 20% by weight, preferably in a range of about 4% to about 15%, more preferably in a range of about 4.5% to about 10%, and most preferably in a range of about 5% to about 7.5% by weight (e.g., about 6%).

Alternatively, when a composition consists essentially of 70% v/v isopropyl alcohol and 30% v/v water, organohalide, and benzocaine so as to not include any components that inhibit penetration, or where when liquid carriers are used that are more penetrating than a mixture of 70% v/v isopropyl alcohol and 30% v/v water (e.g., that include more than 70%, more than about 75%, more than about 80%, more than about 85%, or more than more than about 90% by volume isopropyl alcohol), it may be possible to use smaller quantities of benzocaine while still obtaining a penetration enhancing and kill time increasing effect, such as from about 1% to about 6.5%, preferably between about 1.5% to about 5.5%, and most preferably between 2.1% and about 5% by weight.

In general, the amount of benzocaine should be limited to that amount that increases penetration so as to provide enhanced effectiveness but beyond which increasing amounts of benzocaine do not further enhance penetration and effectiveness but merely prolong the numbing effect. The amount of benzocaine should therefore be less than about 20% by weight, preferably less than about 15%, more preferably less than about 10%, and most preferably less than about 7.5%.

Although less preferred and not as effective as benzocaine in enhancing penetration of penetrating treatment compositions and/or reducing pain without causing undue numbing of a user's lip, other topical anesthetics may be useful in enhancing patient compliance by reducing pain associated with applying penetrating treatment compositions to disordered tissue. Examples of other topical anesthetics include butamben, dibucaine, lidocaine, oxybuprocaine, pramoxine, proparacaine, proxymetacaine, and tetracaine. Of the foregoing, butamben may perform most similar to benzocaine given the similarity in the two chemical structures. In general, such other topical anesthetics can be used in amounts similar to those of benzocaine.

Based on the comparative survey testing that was performed, and in view of the similarity between a wide range of disordered tissues caused by the Herpes virus, it would reasonably be expected that treatment compositions that provided enhanced penetration and treatment of cold sores would also be more effective in treating other disordered tissues caused by the Herpes virus and related viruses, as well as painful disordered tissues caused by bacteria and fungi. Examples include genital herpes, shingles, chicken pox, and forms of Zoster. Other forms of disordered tissue may benefit from this invention as well including cow pox, vaccinia virus, smallpox, and anthrax, *candida albicans*, acne, psoriasis, eczema, seborrhea, dermatitis, and other viral, fungal, and bacteriological tissue disorders. The treatment compositions with enhanced penetration provided by benzocaine are also effective in treating various viral, microbial and fungal disordered tissues. Additionally, disordered tissue caused by non-pathogenic toxins, such as spider venom, as results from spider bites, e.g., venom infections from Brown Recluse spiders and Black Widow spiders, respond well to treatment with the disclosed enhanced penetration treatment compositions.

These and other advantages and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF DISCLOSED EMBODIMENTS

Figure 1:
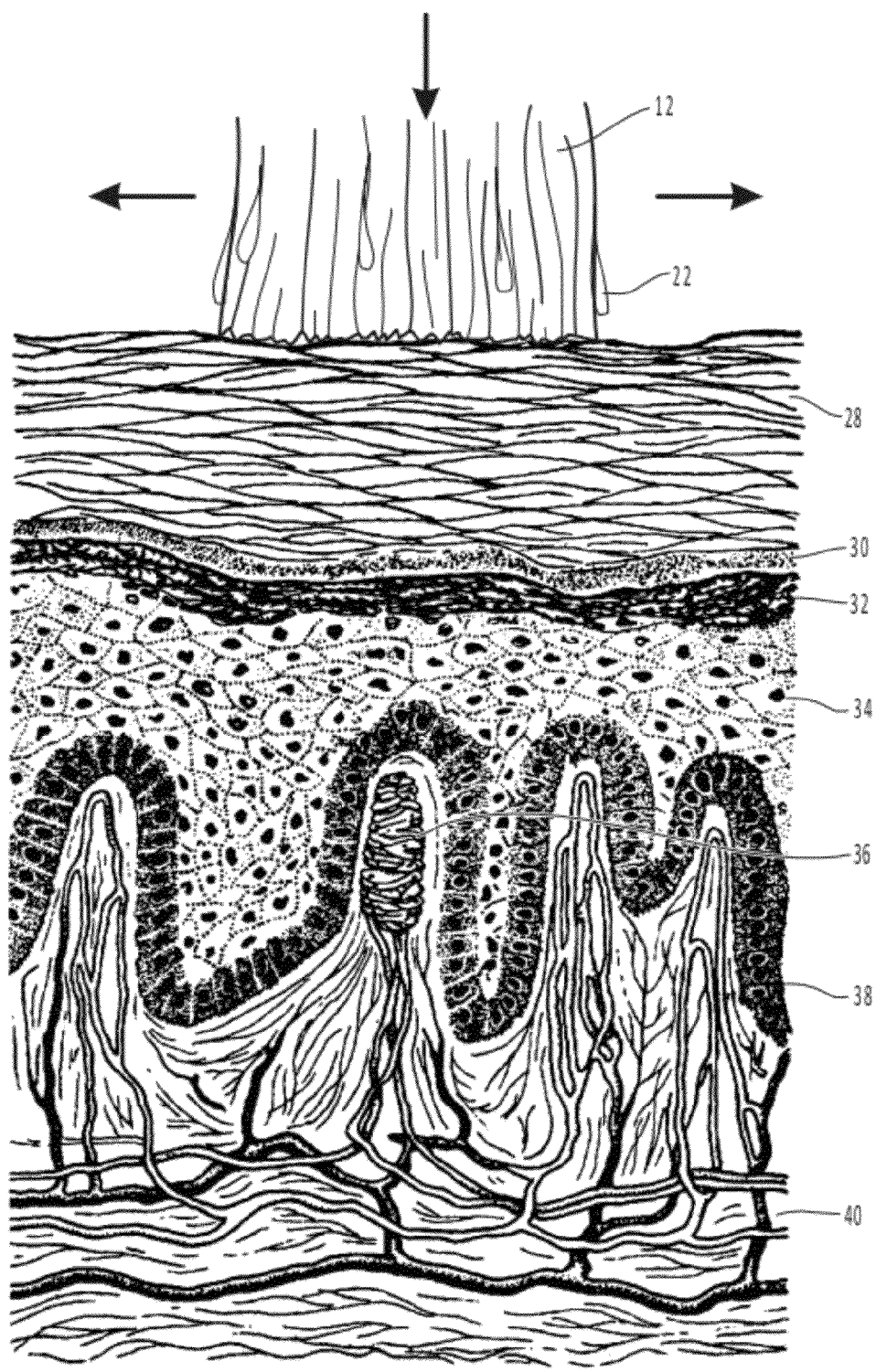
FIG. 1 is a vertical cross-section of the epidermis and the papillae of the dermis.

Embodiments of the disclosure relate to treatment compositions formulated so as to have enhanced penetration and methods for treating disordered tissue using such compositions. The treatment compositions are rapidly absorbed into the disordered tissue, wherein penetration is enhanced as a result of including benzocaine in an amount so as to increase penetration beyond penetration of the treatment composition in the absence of benzocaine. Benzocaine has also been found to increase the residence time of the active agent in the treatment area, which increases kill time.

As a result of enhanced penetration of the treatment composition, coupled with increased kill time and a numbing effect from the benzocaine, effective relief from the pain and discomfort of disordered tissues can most often be achieved after only a single application to the disordered tissue and, at most, 2 or 3 applications. Moreover, the pain associated with the disordered tissue can usually be permanently resolved without recurrence in less than about 10 minutes, 5 minutes, 3 minutes, 2 minutes or even 1 minute after initial application of the composition. The fact that pain is usually resolved and does not recur even after the numbing effect of benzocaine has subsided further emphasizes the increased efficacy of treatment compositions that include benzocaine in specific amounts based on the particular liquid carriers being used.

Finally, the fact that the disclosed treatment compositions can effectively penetrate into and reliably treat disordered tissue with less rubbing or agitation than would otherwise be required if the treatment compositions were devoid of benzocaine is further proof that benzocaine provides a therapeutic benefit beyond simply temporarily numbing pain.

The treatment composition is preferably absorbed into the disordered tissue to such an extent that in less than 1 minute after application the composition can no longer be seen or felt (i.e., the treatment area looks dry and feels dry to the touch). More preferably, the treatment composition is essentially completely absorbed into the disordered tissue in less than about 40 seconds, more preferably less than about 20 seconds, and most preferably less than about 10 seconds. In the case where a dry white residue of benzocaine is present but the surface is otherwise dry, the treatment composition is considered to be essentially completely absorbed into the disordered tissue.

The treatment composition preferably penetrates through the skin to a nerve ending and may cause a penetration sensation at the nerve ending, which is a positive indication that the treatment composition is effectively treating the disordered tissue. The pathway for this penetration is discussed in greater detail below with reference to FIG. 1. After the treatment composition is delivered, optionally with some level of agitation, although agitation may be less than is normally required due the unexpected penetration-enhancing effect of benzocaine, penetration or the sensation of penetration can occur within seconds, e.g., in less than about 5 seconds, 4 seconds, 3 seconds, or even 2 seconds.

FIG. 1 is a vertical cross-section of the epidermis and the papillae of the dermis. FIG. 1 illustrates the stratum corneum 28 disposed upon the fatty layer or stratum lucidum 30. The stratum lucidum is disposed over the stratum granulosum 32. Below the stratum granulosum 32 is the stratum spinosum 34. Typically, the stratum spinosum 34 has a lipid film disposed around each individual cell. Below the stratum spinosum 34 is the stratum basale 38 that overlies vascularized tissue. Within the vascularized tissue the nervous papilla of the corium 36 is located along with blood vessels and nerves 40. FIG. 1 shows a treatment composition being delivered to the stratum corneum 28 in order to allow enhanced penetrating treatment composition 22 to penetrate therethrough. The treatment composition is shown being delivered from an impregnated application pad 12.

The arrows illustrate directions of optional movement of the application pad 12 by way of example. FIG. 1 does not depict application of pressure as the objective is to show the particular layers involved in their natural positions, and once pressure is applied the layers are moved from their natural positions. Treatment composition 22 can penetrate to the nervous papilla of the corium 36 by the penetrating nature of the composition including a liquid carrier and benzocaine to enhance penetration, optionally in combination with agitation. The penetrating activities of the liquid carrier and benzocaine are often sufficient to cause the anti-infective active agent to penetrate through the disordered tissue to a nerve ending, such as the nervous papilla of the corium 36, with much less agitation than would otherwise be needed.

Application of pressure may further increase the ability of the treatment composition to penetrate, as pressure may flatten or compress the layers and assist in forcing the treatment composition downward through the tissue. In any event, penetration to the nerve ending is rapidly accomplished, preferably in several seconds, mainly as a result of the enhanced tissue penetrating effects of benzocaine in combination with a liquid carrier system having penetration properties, such a mixture of water and one or more of isopropyl alcohol, ethanol, acetone, and the like.

While the treatment composition 22 rapidly penetrates to the nerve endings, it is also postulated that the treatment composition resides in reservoir amounts within the stratum spinosum 34 and may continue to diffuse across the stratum basale 38 to the nerve endings over an extended period of time. Pressure may assist in displacing interstitial fluid held within the stratum spinosum, which is then replaced with the treatment composition. When the stratum spinosum 34 is filled with the treatment composition, the treatment composition is available as a bath that continues to kill viruses and destroy inflammatory agents as it slowly diffuses. On this basis, it is desirable to deliver a large quantity of treatment composition into the disordered tissue such that the stratum spinosum 34 is saturated in the region of the cold sore or other disordered tissue for a period that enables the treatment composition to achieve its purpose before it diffuses into the body. For example, the volume applied to a typical cold sore may be in range from about 0.2 ml to about 1 ml, preferably in range from about 0.4 ml to about 0.8 ml and is most preferably about 0.6 ml. Low volumes, such as about 0.2 ml, can work for a single cold sore, especially if the applicator does not retain a significant portion of the treatment composition.

The rate at which the bath diffuses into the surrounding tissue and is replaced by interstitial fluid can be reduced by including benzocaine. Because active agents such as benzalkonium chloride are water soluble, they can be flushed out and displaced by the influx of interstitial fluid back into the treatment area (e.g., stratum spinosum) over time. Benzocaine is soluble within a carrier that includes a tissue penetrating component, such as isopropyl alcohol, but is relative insoluble in water. To the extent that the tissue penetrating component is volatile and selectively evaporates, the relatively insoluble benzocaine is left behind, which can form a barrier that slows down the influx of interstitial fluid, which is aqueous, and thereby slow down the diffusion of active agent out of the treatment area (e.g., stratum spinosum) over time. Thus, benzocaine can enhance initial penetration of the treatment composition in the treatment area and then help maintain the active agent in the treatment area in order to increase the residence time and hence the kill time of the active agent.

Benzocaine, when included in the amounts disclosed herein, can increase residence time of the active agent by at least 5% compared to the treatment composition in the absence of benzocaine, preferably by at least 10%, more preferably by at lease about 20%, and most preferably by at least about 50%. In many cases, the increase in residence time of the active agent is increased by about 20% to about 100% compared to the treatment composition in the absence of benzocaine.

The treatment compositions include at least a biologically active agent, a liquid carrier, and benzocaine in an amount so as to enhance penetration of the treatment composition into disordered tissue. The biologically active agent is selected so as to be effective in treating disordered tissue caused by pathogens (e.g., viruses, fungi or bacteria) or toxins (e.g., spider venom). The liquid carrier is selected to optimally enable the treatment composition to penetrate into the disordered tissue, including through the cell walls of infected and/or infectious cells. The biologically active agents suitable for use in the treatment compositions are set forth hereinbelow and the liquid carriers are described thereafter. Effective amounts of benzocaine are described thereafter, and optional components are also described.

The biologically active agents included in the treatment compositions are preferably anti-infective quaternary ammonium halides and organic compounds that contain at least one carbon-halogen bond. These anti-infective compounds are referred to herein collectively as organohalides, even though some of the anti-infective compounds of this invention do not contain a carbon-halogen bond. Biologically active agents included in anti-infective treatment compositions according to this invention comprise anti-viral organohalides. Benzalkonium chloride is a preferred organohalide. However, other organohalides or quaternary ammonium halide compounds may be used as the active agents in the compositions. Other active agents that are organohalides may include organo-bromides and organo-iodides. Preferably, the organohalides have an alkyl group attached thereto such as a simple $C_nH_{2n+1}$ chain, where n is in a range from 1 to about 50.

The generic chemical structure of benzalkonium chloride is shown below:

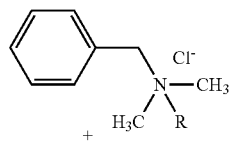

where R=$C_8H_{17}$ to $C_{18}H_{37}$.

As shown, benzalkonium chloride includes a benzene ring and a nitrogen constituent (i.e., a quaternary ammonium group) near the ring. A carbon atom is disposed between the nitrogen constituent and the benzene ring. Two methyl groups and an R group of varying size extend from the nitrogen atom. Suitable benzalkonium chloride may be obtained from many suppliers for example, Spectrum of Gardena, Calif.; Stepan of Northfield, Ill.; Sanofit Pharmaceuticals, Inc. of New York, N.Y. and Mason Chemical of Arlington Heights, Ill.

The term "benzalkonium chloride" as used herein includes compounds in which the alkyl group chain length is within a wide range. A preferred embodiment involves a mixture of compounds with an alkyl chain length distribution that is about 40% $C_{12}$, about 50% $C_{14}$, and about 10% $C_{16}$ (CAS Reg. No. 68424-85-1). Examples of such products include Maquat MC-1412-50%, Mason Chemical Company, 50% activity; Maquat MC-1412-80%, Mason Chemical Company, 80% activity; and BTC-835, Stepan Company, 50% activity. While the foregoing examples satisfy the US Pharmacopoeia requirements for alkyl chain distribution, other alkyl chain distributions are effective against the target lipid coated viruses and other target pathogens. These embodiments are also contemplated within the scope of this invention. These ranges include about 1%-99% $C_{12}$, about 1%-99% $C_{14}$, and about 1%-99% $C_{16}$, and optionally about 1%-99% $C_{18}$. Each manufacturer publishes methods to analyze the bulk substance. Notwithstanding the fact that benzalkonium chloride often refers to mixtures of compounds of varying alkyl chain length, it should be understood that it is within the scope of the invention to utilize a singular benzalkonium chloride compound comprising only one alkyl chain of a particular length.

These anti-infective agents, particularly benzalkonium chloride, are highly effective in killing pathogens (e.g., viruses, bacteria or fungi) or otherwise limiting the source of infections and other complications related to disordered tissue. Also, these anti-infective agents can neutralize or eliminate toxins and inflammatory agents caused by pathogens such as viruses, bacteria or fungi. Rapidly eliminating or neutralizing toxins, inflammatory agents, and their sources results in prompt pain relief.

Benzalkonium bromide and benzalkonium iodide are also examples of suitable organohalides. Benzalkonium bromide has the structure of benzalkonium chloride with the difference being that the chlorine is substituted with a bromine constituent. Analogous considerations apply to benzalkonium iodide. Another example of a suitable organohalide is cetyl trimethylammonium bromide.

Examples of other organochlorides which have anti-infective properties and are suitable for use as the anti-infective organochloride in the treatment composition include benzethonium chloride, methyl benzethonium chloride, cetyl pyridinium chloride, chloroxylenol, hexachlorophene, triclosan, and chlorhexidine. Note that some of the above organochlorides are not suitable for all purposes. For example, benzethonium chloride, chloroxylenol, and chlorhexidine should not be used in a manner which would enable them to be ingested in a toxic quantity.

Additional examples of other organohalides which may be suitable, more particularly quaternary ammonium halides having an alkyl with 6-18 carbons, include: alkyl benzyl dimethyl ammonium halide, alkyl dimethyl ethyl benzyl ammonium halide, n-alkyl dimethyl benzyl ammonium halide, diisobutyl phenoxy ethoxy ethyl dimethyl benzyl ammonium halide, n-($C_{12}C_{14}C_{16}$) alkyl dimethyl benzyl ammonium halide, dodecyl dimethyl ammonium halide, dioctyl dimethyl ammonium halide, dialkyl dimethyl ammonium halide, dialkyl methyl benzyl ammonium halide, octyl decyl dimethyl ammonium halide, lauryl dimethyl benzyl ammonium halide, o-benzyl-p-chlorophenol, dideryl dimethyl ammonium halide, dioctyl dimethyl ammonium halide, and alkyl ($C_{14}C_{12}C_{16}$) dimethyl benzyl ammonium halide. In addition, other known antimicrobial agents may also be used as the active agent or in combination with the active agents provided above, for example, chemicals which are known to act as an antiviral, antibacterial or antifungal agents, such as antifungal agents disclosed by Chodosh in U.S. Pat. No. 5,661,170 and U.S. Pat. No. 5,827,870. Additional examples of effective organohalides include dual quaternary ammonium compounds comprising at least two quaternary ammonium compounds.

One of such embodiments comprises a mixture of n-alkyl dimethyl benzyl ammonium halide and n-dialkyl methyl benzyl ammonium halide. One example of such embodiments is distributed by Stepan as BTC7 776, with a chain length distribution for the n-alkyl of about 60% $C_{14}$, about 30% $C_{16}$, about 5% $C_{12}$, and about 5% $C_{18}$ (CAS Reg. No. 683991-10-5), and a chain length distribution for the n-dialkyl of about 60% $C_{14}$, about 30% $C_{16}$, about 5% $C_{12}$, and about 5% $C_{18}$ (CAS Reg. No. 68391-05-9). Another of such embodiments comprises a mixture of n-alkyl dimethyl benzyl ammonium halide (I) and n-alkyl dimethyl ethyl benzyl ammonium halide (II). One example of such embodiments is distributed by Stepan as BTC 21257M series with a chain length distribution for the n-alkyl in entity (I) of about 60% $C_{14}$, about 30% $C_{16}$, about 5% $C_{12}$, and about 5% $C_{18}$ (CAS Reg. No. 683991-10-5), and a chain length distribution in entity (II) of about 68% $C_{12}$, and about 32% $C_{14}$ (CAS Reg. No. 68956-79-6).

A preferred method of preparing an example treatment composition involves taking 70% isopropyl rubbing alcohol USP (70% isopropanol, v/v, specific gravity 0.877 at 20 C, see 24 USP, p. 927) and then admixing the benzalkonium halide, NF and benzocaine. Isopropyl alcohol USP (IPA) is available from any number of US sources, including Union Carbide, Aldrich Chemical, Texaco, and Shell. Purified water USP is available from a variety of laboratory supply houses, such as Aldrich Chemical, Fisher Scientific, and VWR Scientific. Purified water USP can also be obtained by means of a commercially available water purification system designed to meet the requirements of Purified Water USP.

Embodiments of the present invention include preparations with organohalide concentrations in the range from about 0.001% to about 2% by weight of the treatment composition. These concentration values also refer to preparations that include benzalkonium chloride and where the active ingredient is not benzalkonium chloride, but one of the other substances herein disclosed as active ingredients and equivalents thereof. Furthermore, these concentration values also refer to the combined amounts of active ingredients when more than one active ingredient is present in other embodiments according to this invention, such as when the composition comprises dual quaternary ammonium compounds.

When the anti-infective agent is benzalkonium chloride or other aromatic quaternary ammonium halide compound, the concentration within a topical composition is preferably in a range from about 0.01% and to about 0.5% by weight of the treatment composition, more preferably in a range from about 0.05% to about 0.3% by weight of the treatment composition, and even more preferably in a range from about 0.1% to about 0.2% by weight of the treatment composition. To avoid toxicity, the concentration is less than 0.26% by weight and is more preferably about 0.13% by weight of the treatment composition. Depending on the particular organohalide or quaternary ammonium chloride that is used as the active agent and its toxicity and activity level, the concentration may vary. For example, the concentration may range from about 0.001% to about 2% by weight of the treatment composition.

In one embodiment, the treatment composition consists of only the active agent, such as benzalkonium chloride, the liquid carrier, and benzocaine in a tissue penetration enhancing amount. In other embodiments, the treatment composition consists essentially of the active agent, liquid carrier, and benzocaine, together with other components as described hereinbelow. In any event, the liquid carrier is preferably sufficiently inert with respect to the active agent and any other component present to enable the treatment composition to be stored for long periods of time without deactivating the anti-infective agent, such as at least 1 year and preferably at least 2 or more years.

The liquid carrier preferably has properties that enhance the ability of the treatment composition to penetrate into the disordered epithelial tissue, particularly when used in combination with benzocaine to further enhance penetration beyond the amount of penetration provided by the liquid carrier by itself. The carrier may have a viscosity and/or density which is not significantly greater than that of water in order to optimally enable the treatment composition to penetrate into the disordered tissue. Using a carrier composition having a viscosity which is not significantly greater than water is in contrast to compositions that are coated onto afflicted tissue. Accordingly, the treatment compositions preferably exclude formulations which may be considered to be primarily or essentially gels, creams, lotions, oils, ointments, pastes, emulsions, and viscous colloidal suspensions. It will be appreciated that the liquid carrier may include substances which have either a viscosity or density which is greater than water as long as other substances are also included in the carrier such that the mixture has either a viscosity or density which is not significantly greater than that of water.

The carrier preferably has a tissue penetrating component, such as isopropyl alcohol, that is capable of penetrating the skin and cells in a rapid manner without rapidly diffusing beyond the skin into the body. Benzocaine is included in an amount so as to further enhance penetration of the liquid carrier beyond the ability of the carrier to penetrate in the absence of benzocaine. The treatment composition enables the stratum spinosum 34 illustrated in FIG. 1 to be saturated in the region of the cold sore or other disordered tissue for a period that enables the treatment composition to achieve its purpose before it diffuses into the body. In this way, the treatment composition forms a temporary reservoir (or bath) in the region where it is needed most. In this way, the treatment composition can maximize its effect of killing pathogens and/or destroying toxins within the disordered tissue while minimizing possible damage to surrounding healthy tissues or the organism as a whole.

While isopropyl alcohol is a preferred carrier, other alcohols may also be used. In addition to isopropyl alcohol, ethanol and methanol are also suitable carriers. Benzyl alcohol can be used as a carrier or as an additive as it also acts as a bacteriostat and an anesthetic. Acetone can also be used. Mixtures of the above-mentioned solvents may also be used as desired depending upon the application. As indicated above, however, isopropyl alcohol or ethyl alcohol is preferably used in combination with other carrier constituents. For example, as mentioned above, water may be added to isopropyl alcohol to reduce the pain which may be felt when only isopropyl alcohol is used. Similarly, isopropyl alcohol may be utilized with cetyl alcohol or a combination of cetyl, stearyl, myristyl, or lauryl alcohol and water to reduce the sensation.

Carriers that include isopropyl alcohol and water can have varying ratios depending on the intended use. However, for treating colds sores, the water is preferably included in a range from about 10% to about 50% by volume of the carrier with the remainder being isopropyl alcohol. The water content is more preferably in a range from about 20% to about 40% by volume of the carrier, and most preferably about 30% by volume of the carrier and wherein the isopropyl alcohol is included in an amount of about 70%. Embodiments of preparations according to the present invention may include a carrier that comprises an alcohol, preferably isopropyl alcohol, at a concentration in a range from about 20% to about 90% by volume, preferably in a range from about 40% to about 85% by volume, and more preferably in a range from about 50% to about 80% by volume. The carrier may also include other solvents such as acetone, and the like.

An important issue when applying the treatment composition to a painful cold sore or other disordered tissue is proper compliance by the user. Solvent carriers, such as isopropyl alcohol, ethanol, methanol, acetone, and the like, can cause excruciating pain when applied to sensitive disordered tissues such as cold sores and shingles. Such pain can discourage compliance by the user and undermine the effectiveness of an otherwise effective treatment composition.

It has now been discovered that adding benzocaine in specific amounts to a treatment composition that includes an organic solvent carrier, such as isopropyl alcohol, greatly increases the effectiveness in treating disordered tissues. Unexpectedly, benzocaine, when included in specific amounts, can increase the ability of such treatment compositions to penetrate into the disordered tissue in order for the active agent to more quickly contact and kill viruses or other pathogens within the disordered tissue. Benzocaine can also increase patient compliance by reducing the pain associated with application of the anti-infective composition to painful disordered tissue, particularly with open sores. However, beyond merely reducing pain, benzocaine has been found to increase efficacy of treatment because it promotes faster penetration of the treatment composition into disordered tissue, which reduces the amount of rubbing or agitation that would otherwise be required for the composition to be effective.

The amount of benzocaine within the treatment composition must be high enough to enhance penetration, and preferably help alleviate pain. However, the amount of benzocaine is advantageously not so high as to leave a residue on the surface of the skin and/or cause loss of sensation in surrounding tissue and/or for a prolonged period of time (e.g., greater than about 15 minutes). For example, if included in excessive amounts, benzocaine can cause numbing of a substantial portion of a person's lips for an extended period of time, which can inhibit normal activities such as drinking and talking (e.g., as can occur after a person leaves a dental office after receiving an injection of novocaine).

The amount of benzocaine is most effective when numbing is temporary and goes away once the treatment composition has effectively penetrated into the disordered tissue and resided long enough in the disordered tissue to kill the pathogens and neutralize inflammatory agents in the tissue causing the pain. According to one embodiment, the amount of benzocaine is selected to provide a numbing effect for a time period of about 1 minute to about 20 minutes, preferably about 2 minutes to about 15 minutes, more preferable about 3 minutes to about 10 minutes, and most preferably about 4 minutes to about 8 minutes after numbing first occurs. It is desirable to include an amount of benzocaine so that numbing begins in about 10 seconds or less after application of the treatment composition, preferably in about 8 seconds or less, more preferably in about 6 seconds or less, and most preferably in about 4 seconds or less.

The highly penetrating compositions are formulated, as a result of including benzocaine in combination with a penetrating carrier, so as to penetrate quickly so that the treatment composition is no longer detected on the skin surface after less than about 1 minute, preferably less than about 40 seconds, more preferably less than about 20 seconds, and most preferably less than about 10 seconds. Pathogens are killed and inflammatory agents are neutralized within minutes or seconds after effective penetration such that it is desirable for the numbing effect of benzocaine to subside in less than about 10 minutes after application, preferably less than about 8 minutes, more preferably less than about 6 minutes, and most preferably less than about 5 minutes.

After extensive comparative survey testing supervised by learned health care intermediates, which included obtaining feedback from patients (to whom the benzocaine-containing treatment compositions were administered by the learned health care intermediates), who in this case suffered from painful and highly infective cold sores, it was determined that the most effective amount of benzocaine within treatment compositions that also included a liquid carrier comprised of 70% by volume isopropyl alcohol in water and 0.13% by weight benzalkonium chloride was between about 2.5% and about 7.5% by weight. Above 7.5%, a benzocaine residue was sometimes detected. Below about 2%, benzocaine did not significantly enhance penetration. Between about 2.5% to about 7.5%, however, benzocaine enhanced penetration and caused temporary, but not excessive, numbing when using the treatment compositions that were tested. A more optimal range for this anti-infective composition is about 2.75% to about 6% benzocaine by weight, and the most optimal range was found to be about 3% to about 5% benzocaine by weight.

Nevertheless, depending on the type of carrier that is used, particularly if it is less penetrating than a mixture of about 70% by volume isopropyl alcohol and 30% water (e.g., that includes a less penetrating organic solvent than isopropyl alcohol and/or less than about 50%, or less than about 40%, or less than about 30% by volume isopropyl alcohol), the amount of benzocaine can be increased in order to promote enhanced penetration, and can be as high as 20% by weight, although this amount may cause prolonged numbing (e.g., 1-3 hours). When using a liquid carrier that is significantly less penetrating than a 70/30 v/v mixture of isopropyl alcohol and water, the amount of benzocaine can be included in a range of about 3.5% to about 20% by weight, preferably in a range of about 4% to about 15%, more preferably in a range of about 4.5% to about 10%, and most preferably in a range of about 5% to about 7.5% by weight (e.g., about 6%).

Alternatively, when a composition consists essentially of 70% v/v isopropyl alcohol and 30% v/v water, organohalide, and benzocaine so as to not include any components that inhibit penetration, or where when carriers are used that are more penetrating than a mixture of 70% v/v isopropyl alcohol and 30% v/v water (e.g., that include an organic solvent that is more penetrating into disordered tissue than isopropyl alcohol and/or that include more than 70%, more than about 75%, more than about 80%, more than about 85%, or more than more than about 90% by volume isopropyl alcohol and/or a quantity of DMSO), it may be possible to use smaller quantities of benzocaine while still obtaining a penetration enhancing effect, such as from about 1% to about 6.5%, preferably between about 1.5% to about 5.5%, and most preferably between 2.1% and about 5% by weight.

In general, the amount of benzocaine should be limited to that amount that increases penetration so as to provide enhanced effectiveness but beyond which increased amounts of benzocaine do not further enhance penetration and effectiveness but merely prolong the numbing effect and/or leave a residue. The amount of benzocaine should therefore be less than about 20% by weight (e.g., 2.1% to about 20%), preferably less than about 15% (e.g., 2.2% to about 15%), more preferably less than about 10% (e.g., about 2.25% to about 10%), and most preferably less than about 7.5% by weight (e.g., about 2.5% to about 7.5%).

Although less preferred and not as effective as benzocaine in enhancing penetration of penetrating treatment compositions and/or reducing pain without causing undue numbing of a user's lip, other topical anesthetics may be useful in enhancing patient compliance by reducing pain associated with applying penetrating treatment compositions to disordered tissue. Examples of other topical anesthetics that may be used in addition to or instead of include butamben, dibucaine, lidocaine, oxybuprocaine, pramoxine, proparacaine, proxymetacaine, tetracaine, and mixtures thereof. Of the foregoing, butamben may perform most similar to benzocaine given the similarity in the two chemical structures. Such other topical anesthetics can be included in amounts similar to those of benzocaine. Alternatively, they can be included in an amount between 2.1% and about 15% by weight of the treatment composition, or between about 2.2% and about 10% by weight, or between about 2.3% to about 8% by weight, or between about 2.5% to about 6% by weight. Such other topical anesthetic, either alone or if combined with another topical anesthetic, such as benzocaine, may be included in an amount so as to numb the treatment area for a time period of about 1 minute to about 20 minutes, preferably about 2 minutes to about 15 minutes, more preferably about 3 minutes to about 10 minutes, and most preferably about 4 minutes to about 8 minutes after numbing first occurs. It is desirable to include an amount of topical anesthetic so that numbing begins in about 10 seconds or less after application of the treatment composition, preferably in about 8 seconds or less, more preferable in about 6 seconds or less, and most preferably in about 4 seconds or less.

The carrier may also include other components that, by themselves, may be too viscous to act as tissue penetrating agents, but which, in combination with water, isopropyl alcohol, and other solvents identified herein or known to those of skill in the art, can penetrate tissue. Such components include ethoxylated alcohols (e.g., lauryl alcohol ethoxylates), ethoxylated nonylphenols (e.g., Nonoxynol-9), low molecular weight glycols (e.g., ranging from ethylene glycol to PEG-400, propylene glycol, propanediol, and the like), ethoxylated amines, and their quaternaries. Certain essential oils and emollients, which are normally water insoluble, can be made soluble in water by ethoxylation (e.g., ethoxylated lanolin).

Penetration inhibiting components include chemicals which are petrolatum based substances, materials conventionally utilized as thickeners, naturally occurring oils, substances derived from naturally occurring oils, or any other substance which is added primarily to increase the tendency of a treatment composition to remain on the surface of disordered tissue such as a cold sore. Note that while substances such as petrolatum or thickeners may not be added individually, a component may be added which includes minute amounts of naturally occurring oils or substances derived from oils obtained from natural sources. So, the inventive composition is preferably substantially oil-free, the term "substantially oil-free" means that oil substances are preferably not individually added but may be present due to the natural content of a substance added to the inventive composition. As such, oil may be incidentally present in an amount of less than about 2% by volume, preferably incidentally present in an amount of less than about 1%, more preferably incidentally present in an amount less than about 0.05%, and most preferably in an amount less than about 0.01%.

Treatment compositions may include other components that achieve a particular result and do not substantially reduce the ability of the treatment composition to penetrate into the disordered tissue or the ability of the treatment composition to be anti-infective. Examples of such components include pH adjusters, substances having anesthetic qualities, vasodilators, analgesics and defoamers. Example pH adjustors may include organic acids, mineral acids in minute amounts, organic bases or mineral bases also in minute amounts. Preservatives may be added to the anti-infective composition, including parabens, preferably methyl and propyl parabens. Preservatives, if present, are included in the composition in a range from about 0.0001% to about 0.01% by volume of the treatment composition.

Applicators may form part of a method and system for applying the treatment compositions. As such, applicators may be preconfigured with particular mixtures to treat specific disorders, such as cold sores, chickenpox, herpes zoster (shingles), genital herpes, eczema, and the like. Examples of applicators include those taught in U.S. Pat. No. 5,709,866 (Booras et al.), U.S. Pat. No. 5,704,906 (Fox), U.S. Pat. No. 5,527,534 (Mythling), U.S. Pat. No. 5,016,651 (Stalcup et al.), U.S. Pat. No. 4,887,994 (Bedford), and U.S. Pat. No. 4,952,204 (Korteweg), the disclosures of which are incorporated herein by reference. Example applicators include prepackaged applicators with agitation pads impregnated with the treatment composition. An applicator may be provided as a unitary structure such as a sealed container that is frangible and configured for a single use.

Figure 2A:
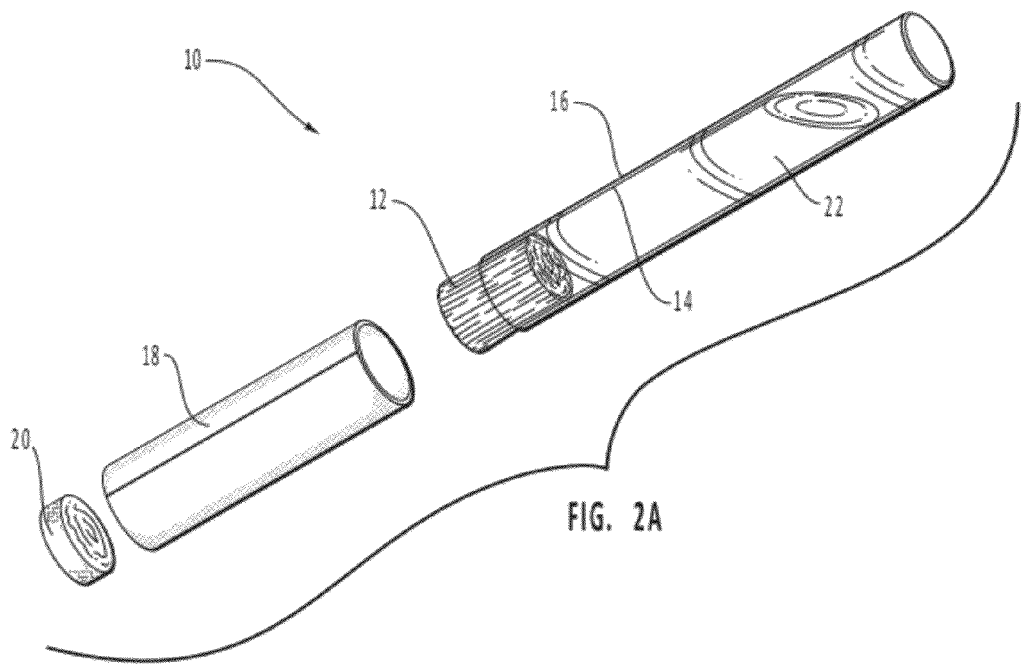
FIG. 2A is an exploded perspective view of an example applicator that contains the treatment composition.

FIGS. 2A-2E depict an example applicator 10. The details of applicator 10 are best seen in FIG. 2A, which is an exploded perspective view, FIG. 2B, which is a perspective view of the assembled applicator, and FIG. 2C as it appears when ready for application. Applicator 10 includes an absorbent pad 12 abutted against a frangible ampule or reservoir 14 via open delivery end 17 of the flexible container 16. Frangible reservoir 14 is housed in a container 16 that forms a holder for pad 12. Frangible reservoir is enclosed by pad 12, the sidewalls of container 16, and the closed end 19 of container 16. Frangible reservoir 14 is preferably a thin glass ampule, while container 16 is preferably formed from a flexible plastic. A protective sleeve 18 is provided, which is designed to keep pad 12 free from contamination until applicator 10 is ready for use on the disordered tissue. A cap 20 is provided to fit into sleeve 18. The treatment composition 22 is held in frangible reservoir 14 until such time as frangible reservoir 14 is broken. One source for applicators having a frangible reservoir and various pad configurations is James Alexander Corporation of Blairtown, N.J.

Figure 2B:
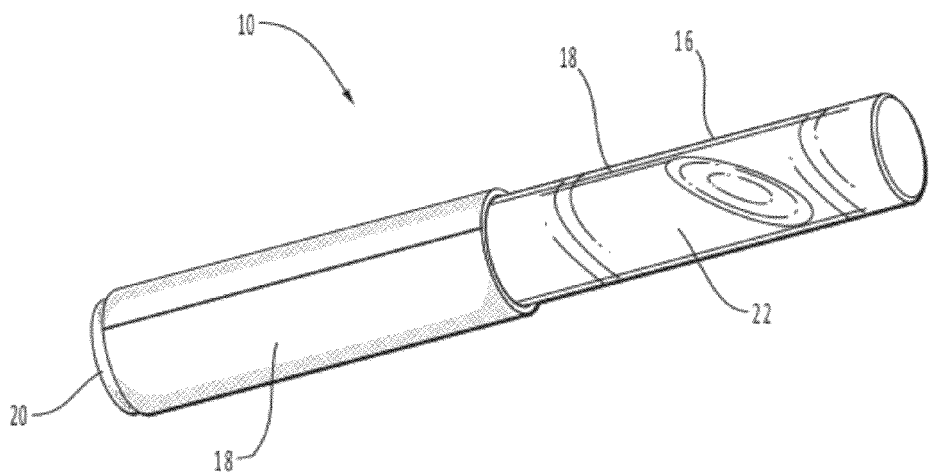
FIG. 2B is a perspective view of the example applicator depicted in FIG. 2A as it appears assembled prior to use.
Figures 2C, 2D:
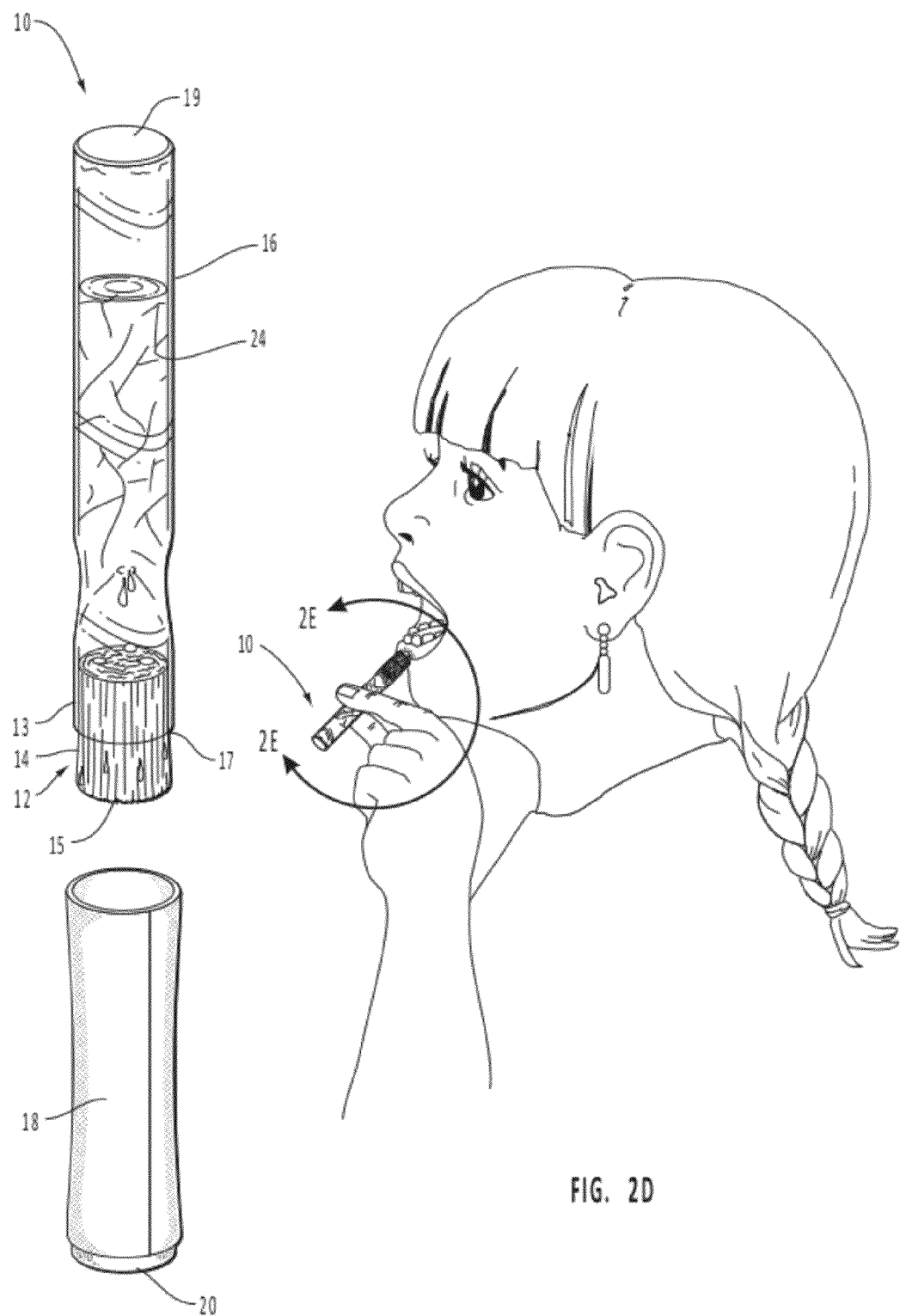
FIG. 2C is a perspective view of the example applicator depicted in FIG. 2B after the glass reservoir is crushed and the treatment composition is allowed to permeate the agitation pad.
FIG. 2D is a perspective view of an individual applying the treatment composition according to the present invention.

FIG. 2C is a perspective view of the applicator depicted in FIG. 2B after frangible reservoir 14 has been ruptured. Treatment composition 22 is allowed to permeate pad 12 in preparation for application to disordered tissue. In FIG. 2C, sleeve 18 has been removed to expose an impregnated pad 12. After impregnated pad 12 is sufficiently wetted, application to the disordered tissue treatment site commences.

FIG. 2D is a perspective view of an individual 26 applying treatment composition 22 to a cold sore at or near the lip according to the present invention. FIG. 2D illustrates that sufficient pressure is being applied against a non-puckered lip as the lip is pressed against the patient's teeth and/or gums in order to direct focused pressure into the disordered tissue while the active compounds are expressed from impregnated agitation pad 12 and into the disordered tissue. The combined effect of vigorous irritation of the disordered tissue and the administration of treatment composition 22 has the result of surprising therapeutic effects.

Figure 2E:
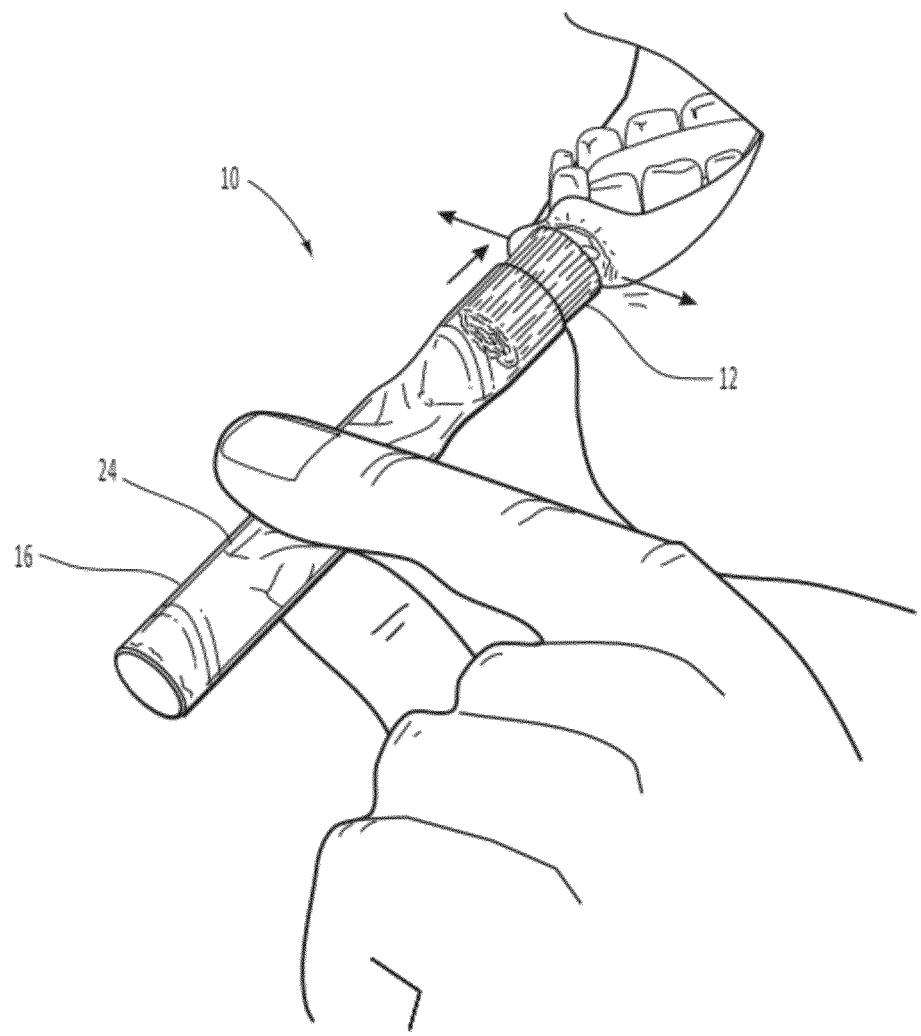
FIG. 2E is a detail taken along the section line 5-5 that depicts a close-up view of the inventive method.

FIG. 2E is a detail taken along the section line 2E-2E in FIG. 2D that depicts a close-up view of an example method of treatment. The detail view more clearly illustrates agitation of the disordered tissue site where impregnated pad 12 is being pressed into the lip in order to be firmly felt at the gums or teeth opposite the disordered tissue. The arrows illustrate directions of movement by way of example.

Once frangible reservoir 14 is ruptured the treatment composition is delivered to pad 12 as gravity enables it to flow into pad 12; however, rupturing frangible reservoir 14 creates shards of glass. Pad 12 prevents shards from passing and causing injury during delivery of the composition to the disordered tissue. Another purpose of pad 12 is delivery of treatment composition. As discussed above, as pad 12 delivers the treatment composition it may be useful to also agitate and/or compress the disordered tissue. Many configurations are available for pad 12, such as those disclosed in U.S. Pat. No. 1,822,566 and France Patent No. 2,700,698.

Figure 2F:
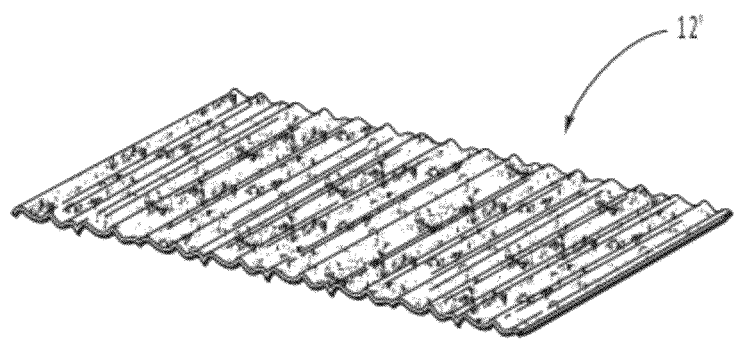
FIG. 2F shows a sheet of material before it is folded or collapsed to form an application pad.

Pad 12 is a folded sheet formed from a web of fibers. FIG. 2F depicts sheet 12' before it has been folded or collapsed to form pad 12. As shown in FIG. 2F, the sheet has a fluted appearance in order to provide an alignment such that when the sheet is gathered together in a bundle, it has longitudinal flutes. These longitudinal flutes provide a flow path for treatment composition 22 while the interlocked web of fibers can prevent shards of glass from passing out of container 16. Pad 12 has a configuration similar or identical to that of a cigarette filter. Examples of cigarette filters configurations that may be utilized are disclosed in U.S. Pat. No. 5,465,739 and U.S. Pat. No. 5,998,500, which are hereby incorporated by reference.

Pad 12 is preferably made of synthetic fibers that have a mesh which enables it to hold treatment composition 22 while having sufficient roughness to allow agitation of the disordered tissue to enhance penetration by treatment composition 22. The fibers forming pad 12 are relatively densely positioned and can be relatively rigid. Pad 12 has a retention portion 13 positioned within flexible container 16. Retention portion 16 is can be attached to flexible container 16 through use of an appropriate adhesive that remains inert in the presence of the treatment composition or through heat fusing retention portion 13 with flexible container 16. Pad 12 also has a delivery portion 14 opposite from retention portion 16 that extends beyond open delivery end 17 of the flexible container 16. Regardless of the configuration of pad 12 or the material from which it is formed, the delivery portion is adapted to deliver the treatment composition to the disordered tissue such that the treatment composition is no longer visibly detectable on the disordered tissue in less than about 1 minute after delivery of the treatment composition onto the disordered tissue, preferably less than about 40 seconds, more preferably less than about 20 seconds, and most preferably less than about 10 seconds.

Delivery portion 17 terminates at an application surface 15 that is relatively flat such that the disordered tissue is uniformly contacted. Uniformly contacting the disordered tissue with the flat application surface 15 reduces the risk of injuring the disordered tissue as the disordered tissue is contacted and agitated.

The retention portion of pad has a length that is sufficient for the pad to be securely anchored in the open delivery end of the container. The delivery portion has a length and sufficient rigidity to enable the application surface to optionally scrub the disordered tissue. When the pad is formed by folding or compressing together a sheet that is a polyester fiber web as shown in FIG. 2F at 12', the retention portion preferably has a length ranging from about 5 mm to about 7 mm and the delivery portion can have a length ranging from about 1 mm to about 5 mm. The length of the retention portion is more preferably about 6 mm and the length of the delivery portion is more preferably 4 mm. The diameter of the pad is preferably about 7 mm to about 1 cm, and is most preferably about 8 mm. This diameter is sufficiently large to enable large amounts of treatment composition to be delivered and provides sufficient surface area to contact a cold sore or other disordered tissue as needed. More particularly, a pad diameter that roughly corresponds with the diameter of a cold sore in its various stages of development is ideally configured to agitate the cold sore treatment site.

In addition to a pad that is a folded sheet formed from a web of fibers, the pad may also be formed from a cluster of aligned bristles. Use of bristles having relatively small diameters is preferred to enable the cluster to scrub while minimizing potential injury to the disordered tissue. For example, if the bristles are formed from nylon and are about 1 cm long so that the retention portion and the delivery portion are each about 5 mm long, the diameter may range from about 0.1 mm to about 0.2 mm, and is more preferably 0.15 mm.

An advantage of applicator 10 is that frangible reservoir 14 holds a relatively large volume of the treatment composition so that the treatment composition is delivered in an amount that is relatively large compared with the surface area to be treated. Further, the delivery is rapidly achieved due to the design of applicator 10 without requiring rewetting of pad 12 as the treatment composition is continually delivered to pad 12 until it is all used. For example, frangible reservoir 14 may deliver about 0.2 ml to about 1 ml to an area that is no greater than about 1 $cm^2$. Accordingly, the volume to surface area ratio is preferably in a range from about 0.2 ml/$cm^2$ to about 1 ml/$cm^2$. Such quantities are ideally sufficient to saturate the stratum spinosum 34 in the region of the cold sore or other disordered tissue so that it is available as a protective bath around the nerve.

A suggested application procedure using applicator 10 is to apply the 0.6 ml of the treatment composition for 30 seconds or longer, preferably while agitating the skin. Typical pain relief is within 5 minutes or less. It may also be advantageous, especially during the prodromal stage, to deliver half of the treatment composition to the cold sore or other disordered tissue for about 30 seconds, wait about 1 minute, and then deliver the remainder for about 30 seconds again. Typically a single application, or at most 2 or 3 applications, are all that is required per outbreak.

Figure 3:
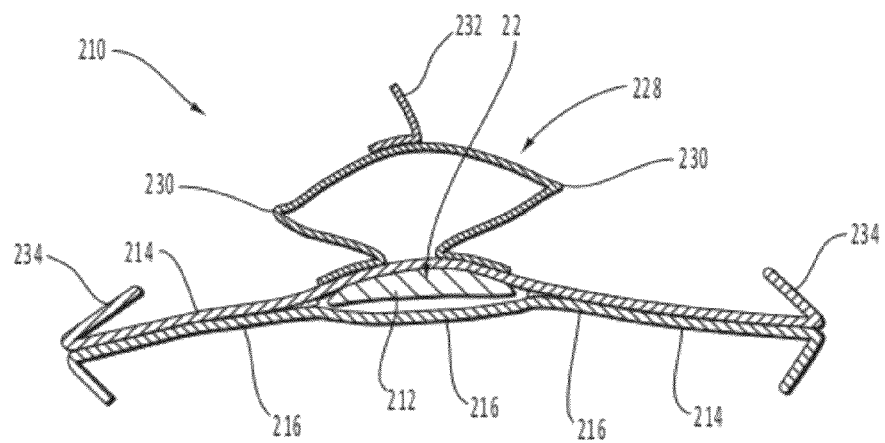
FIG. 3 is an elevational cross section view of an applicator that has a finger loop for vigorous topical irritation of the treatment site.

Another example applicator is illustrated in FIG. 3, which is a cross-sectional elevational view of an applicator 210 including an absorbent pad 212 that may be typical of a sterile adhesive bandage. Applicator 210 also includes adhesive wings 214 that may have adhesive typical of a sterile adhesive bandage. A separate strip acts as a container 216 in order to cause treatment composition 22 to remain in pad 212 until container 216 is stripped away from adhesive wings 214 of applicator 210. In addition thereto, a finger loop 228 that may include finger loop folds 230, and a finger loop tab 232 is attached to applicator 210 immediately above pad 212. Finger loop 228 is configured to lie flat against adhesive wings 214 and can be opened by lifting on finger loop tab 232 and hinge open at finger loop folds 230. Applicator 210 may be applied to a treatment site as typical of a sterile adhesive bandage and left in place indefinitely. Additionally, after a selected time period of having applicator 210 on a treatment site, the medical professional or the patient may grasp the adhesive wing tabs 234 and gently them away from the skin. Meanwhile, the medical professional or the patient may insert a finger into finger loop 228, draw adhesive wings 214 toward finger loop 228, and commence agitating the disordered tissue.

Where it is desired to agitate the cold sore, applicator 210 may be applied at the point of pad 212 onto the disordered tissue and then agitated against the disordered tissue. Thereafter, applicator, 210 may be discarded or adhesive wings 214 may be applied to the patient's skin to allow applicator 210 to remain over the disordered tissue. This alternative may be preferable where bleeding is incidental to the inventive method. As such, applicator 210 doubles as an adhesive sterile bandage.

In summary, applicator 210 may be used for agitation of the disordered tissue or merely as a relatively passive delivery applicator. It may be used initially for application of the anti-infective active agent without agitation of the disordered tissue, followed by agitation of the disordered tissue. Agitation by applicator 210 of the disordered tissue may be alternatively followed by leaving applicator 210 in place like a sterile adhesive bandage.

Figure 4:
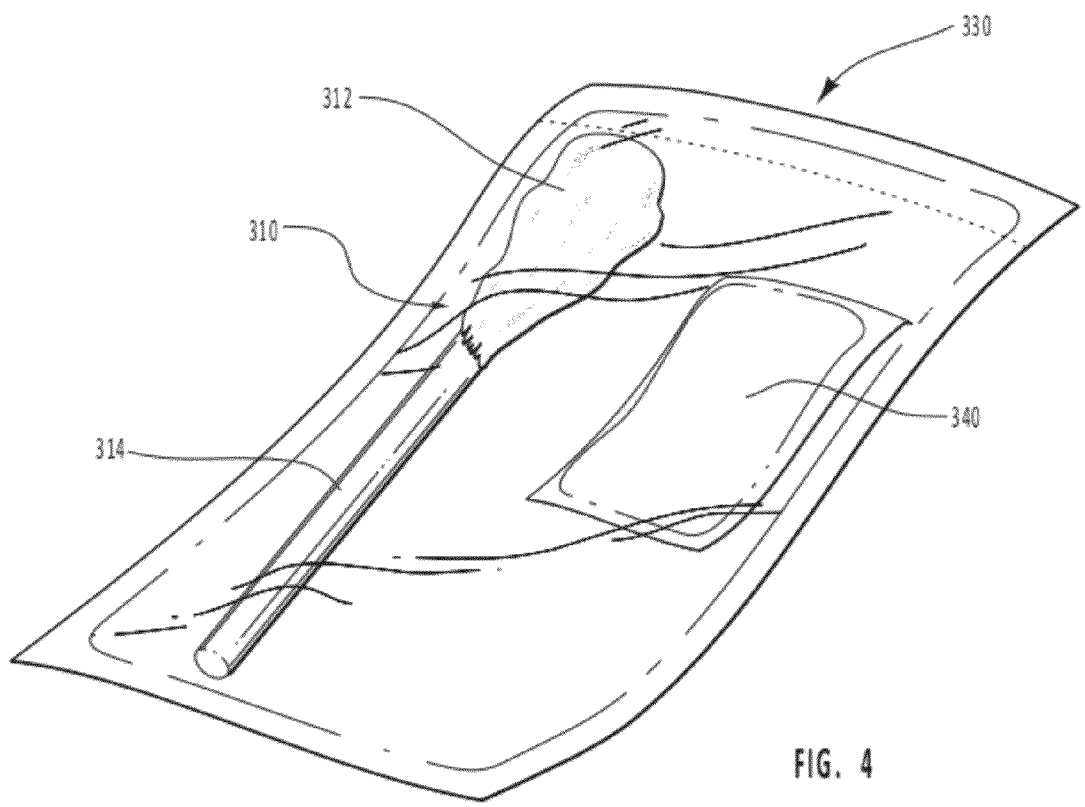
FIG. 4 is an elevational side view of an alternative applicator used in the present invention.

FIG. 4 is an elevational side view of an alternative applicator 310, which includes a swab agitation pad 312 upon a stem 314. Stem 314 may be formed from any suitable material; however, it is preferably relatively rigid to enable agitation pad 312 to be pushed and/or moved in the desired manner. Pad 312 is preferably used such that the side thereof is pushed against the disordered tissue and not the bulbous tip. The side is used so that sufficient pressure can be applied.

It is preferable that swab agitation pad 312 be used under substantially sterile conditions so as to not introduce pathogenic elements into the treatment site of the disordered tissue. The sterile agitation pad of the swab may be dipped into the treatment composition and used to gently abrade the skin. More preferably, the swab is held in a bag as shown at 330, which also holds a burst pouch as shown at 340. Burst pouch 340 holds the treatment composition and is sized and/or positioned within the bag such that upon bursting it can saturate the cotton swab. An example of a bag holding a swab and a burst pouch designed to be frangible is disclosed in U.S. Pat. No. 5,709,866 to Booras, previously referenced.

The swab agitation pad may be replaced with a sponge to gently agitate disordered tissue. An example of a foam pad or sponge mounted on a stick such as stem 314 is disclosed in U.S. Pat. No. 4,887,994 to Bedford, previously referenced. Reference is made to Bedford, col. 2, ln. 44-46, to coarse foam pads. Coarse foam pads enable disordered tissue to be more easily agitated through combined rubbing and application of an appropriate amount of pressure than softer foam pads.

Figure 5:
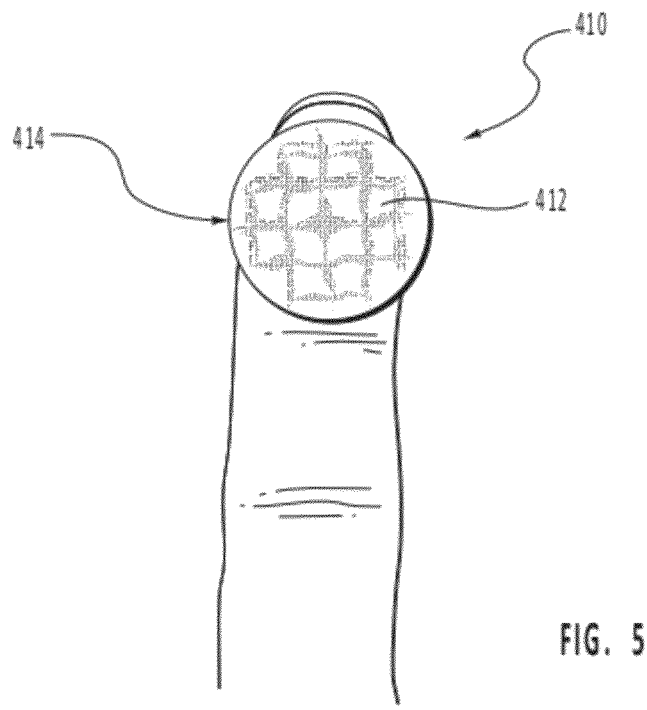
FIG. 5 is an elevational side view of an alternative example applicator that is fixed to a digit for vigorous topical irritation of the treatment site.

FIG. 5 is an elevational perspective view of a fingertip applicator 410, which includes an absorbent pad 412 held on an adhesive surface 414, which can be applied to a fingertip. Pad 412 may include an absorbent material for retaining the treatment composition and it may alternatively contain fixed abrasive elements to assist in agitating disordered tissue.

Figure 6:
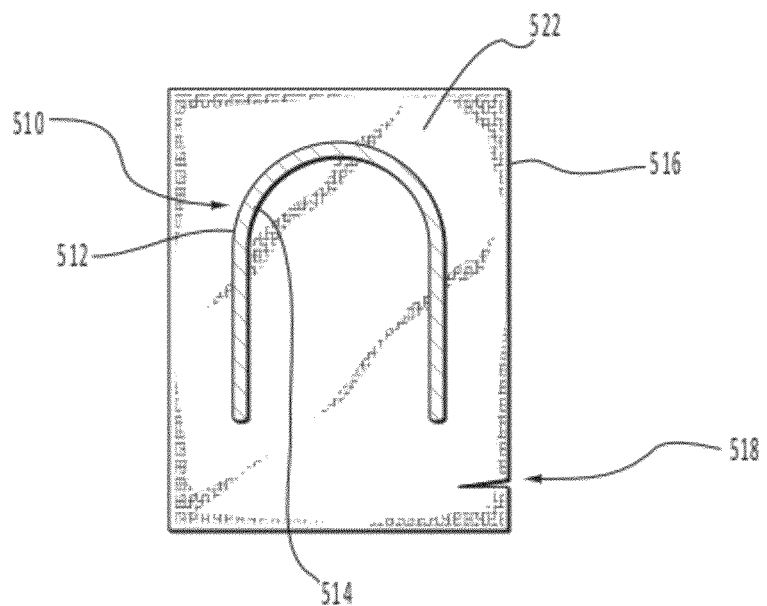
FIG. 6 is a cross-sectional plan view of an alternative example applicator that is placed over a digit and that is contained in a pre-wetted state before use.

FIG. 6 is an elevational cross-section view of a finger- or digit-container applicator 510, which includes an absorbent pad 512 with a first side 512 and a second side 514 that acts as a support. The user may rupture the container 516 such as by tearing a slit 518 and inserting a finger into applicator 510 against second side 514. Container 516 is a bag like that shown at 330 and may be referred to as what is commonly called a pillow pouch or package. Container 516 may also contain a burst pouch. Applicator 510 is preferably pre-moistened by treatment composition 522 within container 516. Applicator may also be held in a container 516 in a dry sterile condition for dipping into a separate reservoir of the treatment composition. First side 512 is made of an absorbent and mildly abrasive material that is substantially uniform in relation to the size of a disordered tissue site. First side 512 can approximate the roughness of a conventional gauze bandage or terry cloth and can be seamless and devoid of fabric folds. Additionally, where second side 514 is used to interface with a finger, it is a support for first side 512 as the delivery portion of applicator 510.

Applicator 510 can have varying sizes depending on its intended use. For example, if applicator 510 is used to deliver the treatment composition to a cold sore it is large enough to permit entry of at least one fingertip into it. However, if applicator 510 is used to treat fingertip sores caused by shingles on, for example, an individual's back or large surface, it may be useful for applicator 510 to be large enough so that several fingers or even the entire hand can fit inside it like a mit. A mit-sized applicator enables the treatment composition to be rapidly delivered to large surface areas.

Figure 7:
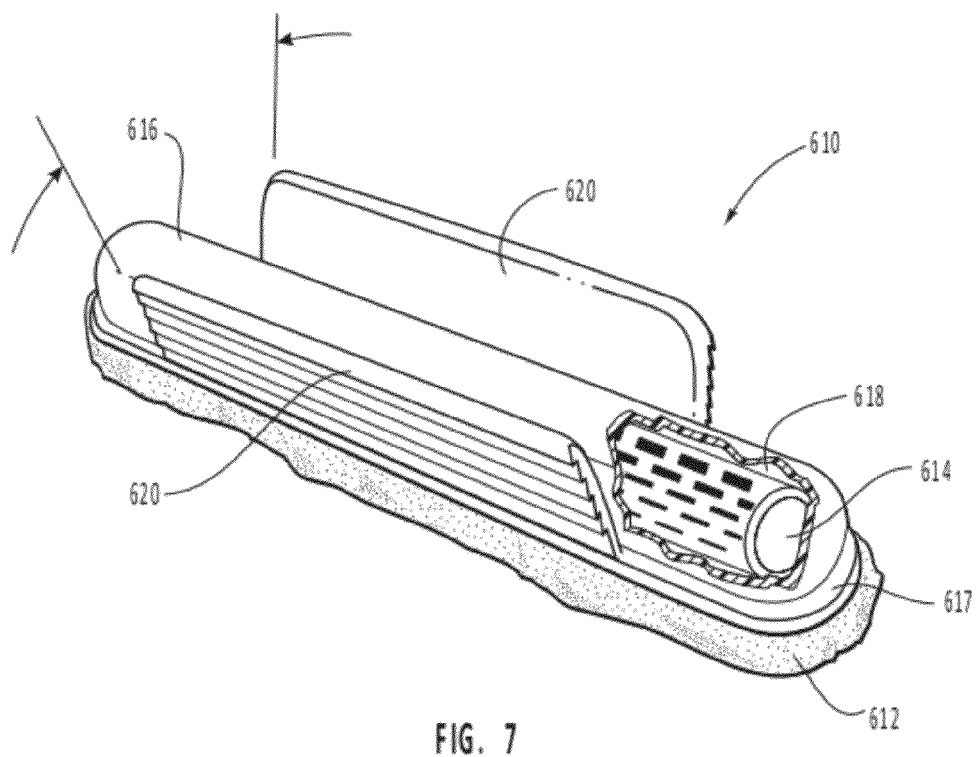
FIG. 7 is a perspective view with a partial break-away view of an alternative example applicator that is used to apply the treatment composition to large surface areas of the body.

FIG. 7 depicts another embodiment of a delivery system. Like the mit sized version of applicator 510, applicator 610 is useful for treating large surfaces such as a patient's back. Applicator 610 comprises a treatment composition in a large frangible ampule 614 or reservoir, a container 616, and a pad 612. Container 616 has thin walls at recess 618, the closed end opposite from open delivery end 617, into which frangible ampule 614 is positioned.

When applicator 610 is ready for use, handle wings 620 are squeezed until they compress the thin sidewalls of container 616 inward at recess 618 such that pressure is applied to frangible ampule 614 and ampule 614 ruptures. The treatment composition is then released and flows into pad 612. Frangible ampule 614 can contain a volume of treatment composition ranging from about 0.5 ml to about 4 ml, preferably from about 1.5 ml to about 3 ml, and more preferably from about 2 ml to about 3 ml.

Figure 8:
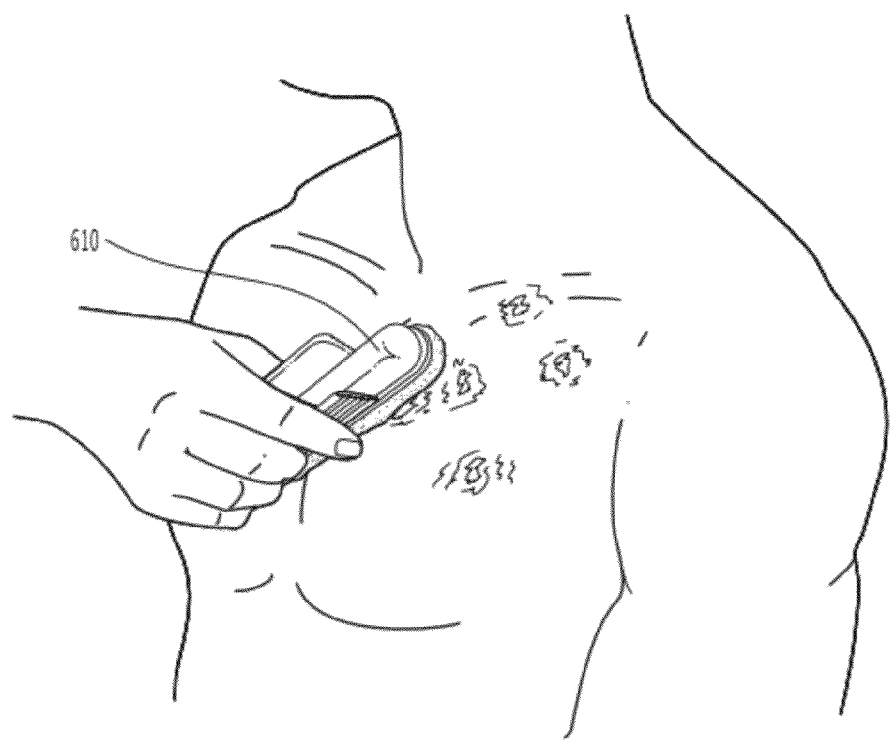
FIG. 8 is a perspective view of the example alternative applicator in FIG. 7 being used to apply the treatment composition to sores from shingles on the chest area.

Pad 612 is adhered to the rim of open delivery end 617 of container 616 by suitable means, such as an adhesive, heat fusion, or a mechanically interlocked configuration. Pad 612 prevents shards from the rupture ampule from passing through and causing injury. Once, pad 612 is adequately moistened, it can be used to rapidly apply treatment composition to large surface areas as shown in FIG. 8, which depicts the use of applicator 610 to apply the treatment composition to a patient's chest afflicted with sores from shingles. Applicator 610 can be used to merely deliver the treatment composition or it can be used to apply pressure and/or scrub the treatment area.

Figure 9:
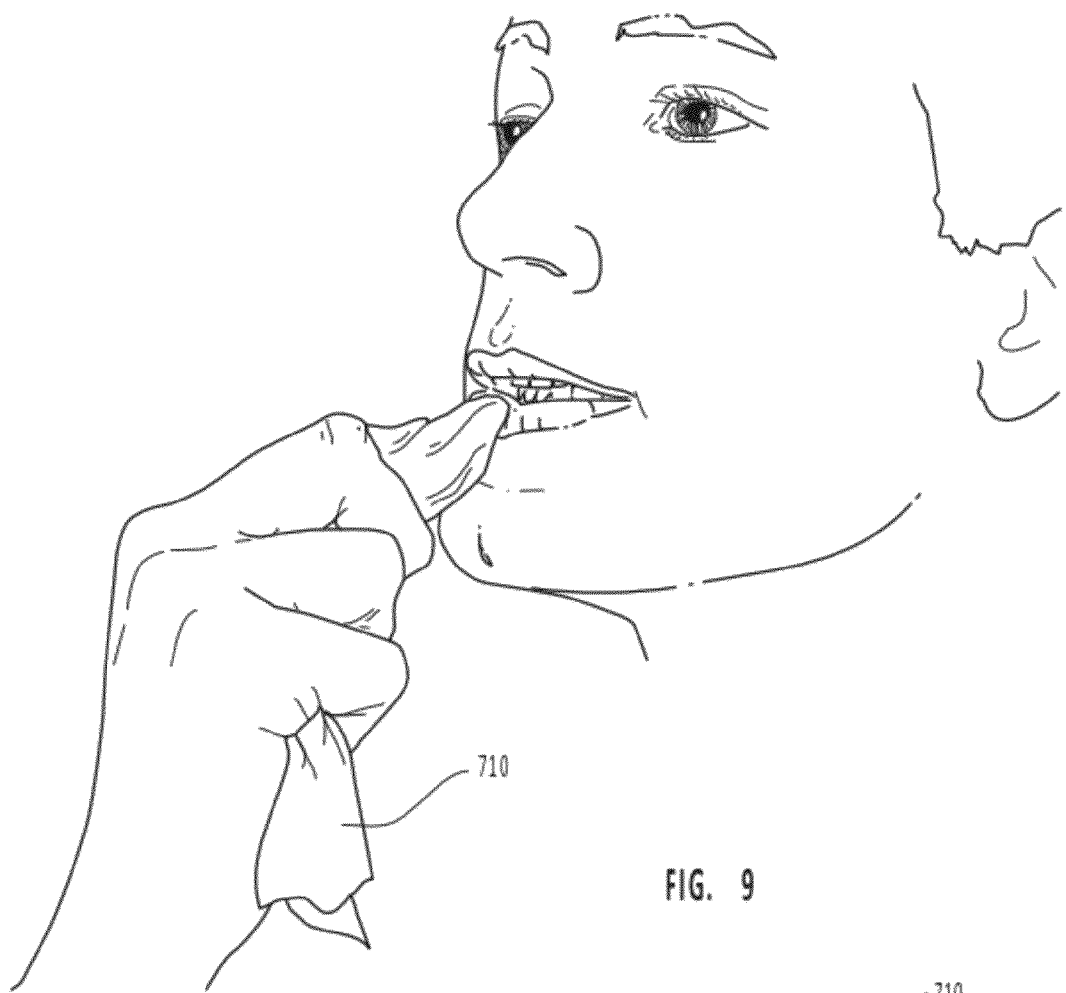
FIG. 9 is a perspective view of an example towelette used to apply the treatment composition to a cold sore.
Figure 10:
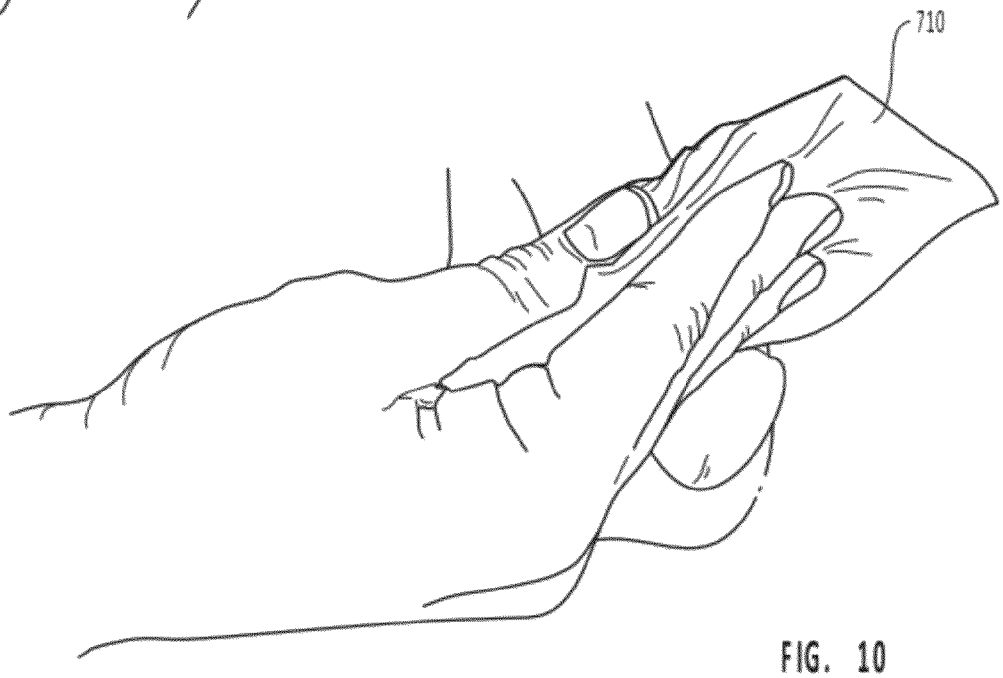
FIG. 10 is a perspective view of an example towelette used to apply the treatment composition to a sore on male genitalia.
Figure 11:
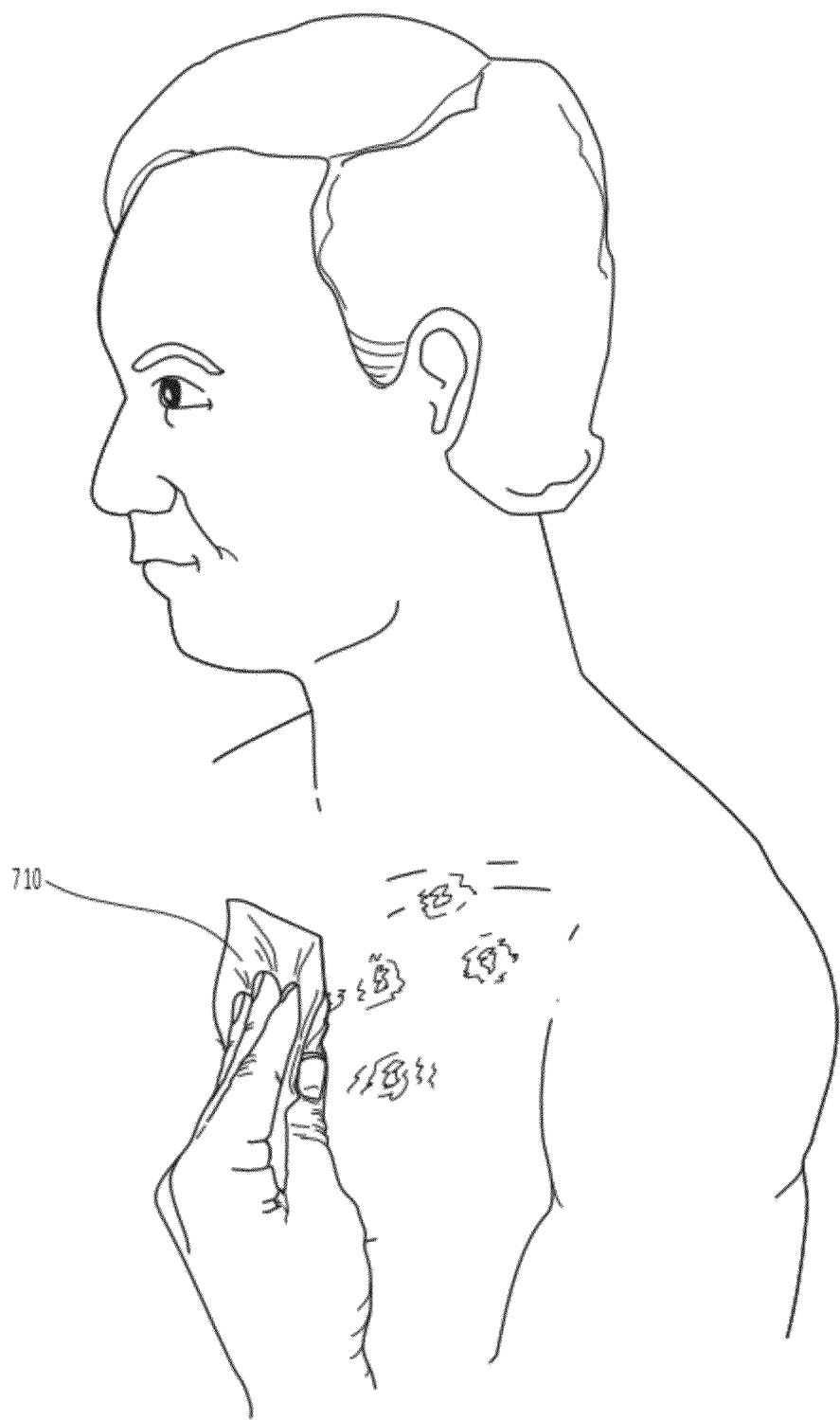
FIG. 11 is a perspective view of an example towelette used to apply the treatment composition to sores from shingles on the chest area.

FIGS. 9-11 depict a towelette being used as an applicator to treat various disordered tissue. The towelette depicted at 710 may be relatively smooth or relatively abrasive and can have varying thickness. The towelette can be repeatedly dipped to rewet it. For example, FIG. 9 depicts a user with a finger wrapped in a towelette used to deliver the treatment composition to a cold sore on the user's lip. The towelette may be formed from fibers such as those discussed above in reference to applicator 10 or any of the other applicators. The towelette may be selected from existing stock formed from treated natural fibers, synthetic fibers, and untreated natural fibers. One example of an abrasive towelette is a rough paper towel used in the paper towel industry or the like. One of ordinary skill in the art may select a towelette that has the preferred abrasive qualities while maintaining a preferred absorbability in order to convey the anti-infective active agent to the disordered tissue treatment site.

FIG. 10 depicts towelette 710 being used in the genital area. An advantage of using a towelette for delivering the treatment composition in the genital area is that the towelette is able to conform to the various surface features and it enables the user to deliver the composition with sensitivity to the more sensitive parts in the genital area of the body. As with the other applicators, the towelette is disposed of after a single use to prevent the spread of substances contained in the disordered tissue.

FIG. 11 depicts towelette 710 being used to deliver the treatment composition to a patient that has sores from shingles on his chest. Towelettes are ideal for areas of the body that have surfaces areas that are not primarily flat or that have irregular surfaces such as the genital area. The towelette is ideal for these areas as it can access all areas without causing pain.

The towelette may be held in a bag such as the bag shown at 330 which also holds a burst pouch as shown at 340. Burst pouch 340 holds the treatment composition and is sized and/or positioned within the bag such that upon bursting it saturates the towelette. The bag may hold the towelette and the burst pouch in a similar fashion to the designs disclosed in U.S. Pat. No. 5,709,866 to Booras, previously referenced. Towelette 710 may be dipped into a separate reservoir and then used to deliver the treatment composition.

An example method of treating disordered tissue includes impregnating an applicator with the treatment composition and contacting the treatment site with the applicator. Though rigorous agitation is not required, moderate to gentle agitation of the disordered tissue may be useful as the induced physical trauma can cause awakening of the body's immune response local to the irritation. As such, the immune response and the penetration of the inventive composition into the disordered tissue has the concerted effect of a rapid decline of the infection. Nevertheless, the enhanced penetration of treatment compositions that include benzocaine reduces or eliminates the need to agitate the disordered tissue to obtain effective treatment.

Chemotaxis, the migration of phagocytes such as granular leucocytes and human leucocyte associated (HLA) antigens to an area of a tissue disorder, may be enhanced and assisted by agitation of disordered tissue with the enhanced penetration treatment composition. The combination of the anti-infective active agent, preferably benzalkonium chloride, with the chemotaxis phenomenon caused by agitation of the disordered tissue, has the unexpected effect of rapid decline of infectant such as a virus or a microbe in the disordered tissue. One type of granular leucocyte, the neutrophil, has the ability to activate defenses which are amino acids that exhibit a broad range of antibiotic activity against bacteria, fungi, and viruses. Consequently, the synergistic effect of agitation is rapid delivery and awakening of immune response. The neutrophil, if activated, is useful to treat disordered tissue according to the present invention where bacteria, fungi, or virus infections occur. Further, agitation causes fluids to concentrate in the area of the disordered tissue, which further enables the active agent to penetrate effectively.

EXAMPLES

The following examples are provided in order show how including benzocaine in various amounts can enhances penetration of treatment compositions comprising an organohalide anti-infective agent and a liquid carrier. It should be understood that the following examples are given by way of example only and not by limitation. Given the effects and trends shown the examples, one of ordinary skill in the art will readily understand that virtually any treatment composition within the scope of the disclosure can have enhanced penetration when combined with an appropriate amount of benzocaine as described above, which is selected for use in combination with a given liquid carrier having a particular native propensity to penetrate a targeted disordered tissue.

Comparative Study

A comparative study was performed by retrospective written survey by participants comparing the efficacy of original formula Viroxyn® (isopropyl alcohol tincture of benzalkonium chloride, 0.13%) versus Viroxyn® professional with benzocaine (isopropyl alcohol tincture of benzalkonium chloride, 0.13% and 5% benzocaine) in the treatment of herpes labialis outbreaks in consumers with naturally occurring classical cold sores who have experience in the use of both products and using participant reported outcomes of untreated cold sore lesion outbreaks as the control.

The study examined the primary outcome variables of time-to-healing (loss of hard scab and return to intact skin) and time to loss of discomfort (a persistent report of mild or none). The hypothesis of "No Difference" was used to test for differences in study drug outcomes.

A retrospective written survey was conducted using participants who were experienced in the use of both products (n=118). While the retrospective survey design employed in this study may have limitations, the potential for both investigator and patient bias, and subsequent study confounding, have been identified as being impossible to manage in a prospective clinical study. Thus, a retrospective study may be the only credible way to study these two drugs in a head-to-head manner. Simple descriptive statistics (mean, median, standard deviation) were employed. Differences between cohorts were measured using T-test.

The results of this study show a dramatic difference in outcome versus untreated cold sores with both drugs performing well against untreated cold sores (Control). Further examination shows a better outcome using Viroxyn® Professional with 5% benzocaine (n=118), than using original formula Viroxyn® (n=118) with no benzocaine. The differences in time to healing are dramatic, statistically significant, and clinically relevant, with the Viroxyn® Professional with 5% benzocaine cohort showing a median 6.0 day reduction in time-to-healing versus the Control ($p<0.01$) and the original formula Viroxyn® cohort showing a median 5.0 day reduction in time-to-healing versus the Control ($p<0.01$). A direct comparison of the time to healing outcomes of the two drugs shows Viroxyn® Professional with Benzocaine median time to healing of 4.0 days versus the original formula Viroxyn® median time to healing outcome of 5.0 days ($p=0.02$). A similar result was seen in time to loss of discomfort with the Treatment cohort (Viroxyn® Professional with benzocaine) reporting loss of symptoms in a median 2 minutes and the Comparator cohort (original formula Viroxyn®) showing loss of symptoms in a median 10 minutes versus a median 5.0 days (7200 minutes) of discomfort in the Control group ($p<0.01$). This is significant given that the loss of discomfort must remain persistent and the effect of the benzocaine component in the treatment drug is short lived. A direct comparison of the Viroxyn® Professional group versus the Viroxyn® group was significant as well ($p=0.05$).

Both Viroxyn® and Viroxyn® Professional with benzocaine have been well received in the dental healthcare profession. Initially, the decision to reformulate Viroxyn® to contain benzocaine was intended to alleviate consumer complaints of extreme discomfort in applying the medication. Upon reformulation, the incidence of discomfort did abate. However, there were nearly immediate reports of increased overall satisfaction with Viroxyn® Professional with benzocaine and reports of increased efficacy versus the original formula Viroxyn®. Consumers noted that the numbing effect of the benzocaine took place very quickly and, unexpectedly, they experienced increased efficacy with less rubbing and/or less intense rubbing compared to original formula Viroxyn®.

The purpose of this study was to compare these two products designed for OTC usage relative to time of the healing process to learn if one is superior to the other both in terms of time to healing and in time to participant loss of discomfort. Due to the design of the study, and the importance of measuring any such differences using sufficient numbers to be convincing, sufficient time in the marketplace with Viroxyn® Professional with benzocaine was needed so that a larger study population of persons experienced in using both drugs, more typical of scientifically sound human clinical studies, would be available.

The "Gold Standard" for a drug study typically includes multiple study sites, randomization, double blinding, and placebo control. However, for OTC products that have become familiar to the public, keeping study participants from becoming aware of which OTC drug they have been assigned may not be possible. Newly issued FDA Guidance documents (December 2009 & March 2010) provided the basis for the study design. Clinical trials based on patient reported outcomes are now being accepted by FDA as pivotal trials. There are several key provisions of such clinical trials. First, the study participant must directly report the outcome metrics on a suitable instrument without input or filtering from any healthcare professional. This means that paper or electronic surveys, diary cards, etc. are sent directly to the investigators. Second, there is a reasonable expectation that the participant has a good memory of the outcome, i.e., the patient was not under anesthesia, does not suffer from a disease or condition that affects the participant's memory, etc. Third, the measurements under study are clinically relevant to the disease, and can be self-evaluated by the layman. The Comparative Study used a design that is in accordance with the new FDA Guidance Documents.

The primary outcome objectives that were studied were: 1) time to persistent resolution of discomfort (pain, itching, and burning) and 2) time-to-healing (loss of hard scab and return to intact skin). These outcomes were studied for both drugs versus Control (untreated lesions) and head-to-head against each other. Participants were selected from a list of persons who had used both Viroxyn® (Comparator) and Viroxyn® Professional with benzocaine (Treatment). It was anticipated that some participants would have more than one member of a household that used Comparator, Treatment, or both, and would submit a separate survey. All surveys were returned directly to the investigators and data entries were made by one person and verified by a second person. In accordance with the study protocol, surveys that included data for one drug, but no data for the other, were not analyzed in that "intent to treat" was not triggered. Surveys returned with some data present for each drug, but missing other data, triggered the protocol imputation rule of "assign all missing data the median value".

Participant natural history was gathered for use as the Control. A 4-point discomfort scale was provided as was used in similar studies. Time to healing was given as whole days. If participants entered a range (e.g., 10-12 days), the lower number was used in the study. The survey asked the following:

Initials, Age, Gender, Race
How many cold sore do you get per year?__
How much discomfort (pain, itching, or burning) without treatment when the cold sore is at its worst?
_ None
_ Mild (I hardly notice it)
_ Moderate (I am very aware of the discomfort)
_ Severe (I find it hard to concentrate, work, or sleep)
How long until the scab falls off without treatment?_ days
How long until the pain is down to mild or none?_ days Page two of the survey asked the patient to indicate the time to persistent loss of discomfort when using Treatment and when using Comparator to treat a cold sore. The time intervals were presented as multiple-choice to standardize responses. Potential selections included 1 minute or less, 2-10 minutes, 10-30 minutes, 30-60 minutes, 1-2 hours, 2-4 hours, 5-10 hours, and 11+ hours. Page two of the survey also asked the patient to indicate the time-to-healing (loss of hard scab and return to intact skin) when using Treatment and when using Comparator drug to treat a cold sore. The time intervals were presented as multiple-choice from 1 day to "13 days or more" in one day increments to standardize responses.

All participants who returned a survey with at least one data point showing outcome data for each drug were treated as "intent-to-treat" and the data submitted was included in the analysis. Simple summary statistics (mean & standard deviation) were provided for demographical information. Differences in age between male and female participants were analyzed using t-test, 2-tailed, equal variance. Time-to-healing and time to loss of discomfort were compared to Control and subsequently head-to-head for the two study drugs using t-test, 2-tailed, equal variance. The hypothesis of "No Difference" was used to analyze potential differences in primary outcomes for both groups. With regard to simple descriptive statistics, most scholarly papers describing time-to-healing outcomes observed in clinical studies of herpes labialis rely on the median value for time-to-healing as this tends to negate the effects of out-lying data and often because the data are not normally distributed.

In the comparative study, the outcome data is presented as median value and as mean value+standard deviation (Std. dev.). Statistical significance is expressed as "p". A p-value of >0.05 confirms the null hypothesis of no difference between groups. A p-value of <0.05 invalidates the null hypothesis of no difference and confirms a statistically significant difference between the two groups being measured.

The participant reported outcome results were as follows. All surveys returned with at least one data entry were analyzed as "intent-to-treat". The survey sample was n=137 and the distribution of responses strongly favoring those who had experience with the use of both products were as follows, wherein each number was sufficiently large enough to "power" the respective portions of the study.

Supplied data for both Viroxyn & Viroxyn Professional: n=118 (86.2%)
No data for Viroxyn: n=4 (2.9%)
No data of Viroxyn Professional: n=15 (10.9%).

It will be noted that a significant number of participants did not trigger "intent to treat" for at least one treatment group. It is easily seen that total censoring of the data for these individuals is more appropriate than assigning all the median value. Using that imputation rule would unfairly introduce bias in favor of the Viroxyn® Professional with benzocaine group given the dissimilarities in median outcome for the two groups. The demographics of the group with experience using both products favored women over men, and Caucasians over other races, but the differences in ages of the groups were not statistically significant. No conclusions can be drawn from the skew toward women and Caucasians. The demographics for n=118 were as follows:

Male: n=44 (37.3%); Mean Age+std. dev.: 44.2±13.2 years
Females: n=74 (62.7%); Mean Age+std. dev.: 44.2+11.1 years
Age; Male vs Female p=0.99*
Caucasian: n=114 (96.6%)
Black: n=1 (0.9%)
Hispanic/Latino: n=1 (0.9%)
Asian/Other: n=1 (0.9%)
Native American n=1 (0.9%)

The time to healing is defined as loss of hard scab and return to intact skin. The number of cold sores per year shown below is consistent with the literature values from other placebo controlled human clinical trials. Participants reported that both Comparator and Treatment demonstrated a time-to-healing advantage over Control and the differences are statistically significant (p<0.01). This finding was expected for Viroxyn® or Viroxyn® Professional with benzocaine. However, the "Null Hypothesis of No Difference" is not valid when participant reported time-to-healing using Viroxyn® Professional with benzocaine is compared to that using original formula Viroxyn®. The differences are both statistically significant and clinically significant and strongly favor Viroxyn® Professional with benzocaine.

Participants reported a median 5.0 and mean 5.1+2.7 days time-to-healing using original formula Viroxyn® versus a median 4.0 days and a mean 4.3+2.4 days time-to-healing using Viroxyn Professional with Benzocaine (p=0.02) and versus a median 10.0 and mean 11.3+4.3 days time-to-healing of Control (p<0.01 for both treatments). The Control outcome data compares favorably to other studies.

The participant reported outcomes (time to healing in days) for n=118 (loss of hard scab and return to intact skin) were as follows:

|  | median | mean ± std. dev. |
| --- | --- | --- |
| Number of Cold Sores per year: | 4.0 | 4.6 ± 4.0 |
| Participant Reported Time-to-healing: | | |
| Control: | 10.0 days | 11.3 ± 4.3 days |
| Viroxyn ® | 5.0 days | 5.1 ± 2.7 days |
| Viroxyn ® Professional with Benzocaine | 4.0 days | 4.3 ± 2.4 days |

1. p < 0.01 for a comparison of Control vs. Viroxyn ®
2. p < 0.01 for a comparison of Control vs. Viroxyn ® Professional with benzocaine
3. p = 0.02 for a comparison of Viroxyn ® vs. Viroxyn ® Professional with benzocaine The additional 1 day advantage of Viroxyn® Professional with benzocaine versus Viroxyn® is statistically significant (p=0.02) and clinically significant. Other herpes treatment drugs have been approved by FDA for showing less than one day improvement versus control (e.g., Abreva). Thus, the median 1.0 day advantage in time to healing is indeed clinically significant.

The time to loss of discomfort is a persistent report of none or mild on the 4-point pain scale. Participants reported that both Treatment and Comparator demonstrated a time to loss of discomfort advantage over Control and the differences are statistically significant (p<0.01) and clinically significant. This finding again was expected. However, the "Null Hypothesis of No Difference" is not valid when participant reported time to loss of discomfort using Viroxyn® Professional with benzocaine is compared to that using the original formula Viroxyn®. Viroxyn® Professional with benzocaine demonstrated a median 2 minute time to loss of discomfort versus a median 10 minute time to loss of discomfort using Viroxyn®. When the mean values are taken into account, the differences are more dramatic with Viroxyn® Professional demonstrating a 30 minute time to loss of discomfort and the original formula Viroxyn demonstrating a 60 minute time to loss of discomfort. These differences are both statistically significant (p=0.05) and clinically significant.

The participant reported time to loss of discomfort (persistent report of mild or none) for n=118 were as follows:

|  | median | mean ± std. dev. |
| --- | --- | --- |
| Control | 5.0 days | 6.3 ± 3.4 days |
| Viroxyn ® | 0.167 hours (10 minutes) | 1.0 hour ± 2.3 hours (60 minutes) |
| Viroxyn ® Professional with benzocaine | 0.033 hours (2 minutes) | 0.5 ± 1.7 hours3 (30 minutes) |

1. p < 0.01 for a comparison of Control vs. Viroxyn ®
2. p < 0.01 for a comparison of Control vs. Viroxyn ® Professional with benzocaine
3p = 0.05 for a comparison of Viroxyn ® vs. Viroxyn ® Professional with benzocaine.

It should be understood that the study design-induced bias favors original formula viroxyn. The maximum reportable time to healing value of "13 days or more" was assigned a value of 13. That means the time to healing outcomes of more than 13 days were effectively censored at 13 days. Four (4) times as many participants reported this value when reporting their time-to-healing when using original formula Viroxyn® (n=4 or 3.4% of respondents) versus Viroxyn® Professional with benzocaine (n=1 or 0.85% of respondents). It is reasonable to assume this bias is real and had a significant effect that favored the original formula Viroxyn® by cutting short the 4 reports of 13 days or more. The further beyond 13 days the report may have been, the more the bias favors original formula Viroxyn® and thus the observed differences are the more credible.

A similar study design-induced bias is seen in participant reported time to loss of discomfort. The designation "more than 11 hours" was assigned the value of 11 hours, effectively censoring all data of outcomes lasting more than 11 hours. Like the study design-induced bias demonstrated above, the original formula Viroxyn® drug group had a larger number of respondents reporting "more than 11 hours" (n=3 or 2.5% of respondents) versus the Viroxyn® Professional with benzocaine group (n=1 or 0.85% of respondents). Like the time to healing values, the further beyond 11 hours the reported data may have been, the more the bias favors original formula Viroxyn® and thus any observed difference become all the more credible.

With respect to memory bias in reporting untreated cold sore data, any tendency to overstate the severity and/or duration of an untreated cold sore event will favor the less effective drug, which in this study was the Comparator drug (original formula Viroxyn®). However, as previously mentioned, the fact that the Control group time to healing value corresponded so favorably to the placebo time to healing values in other cold sore studies found in the peer-reviewed literature offers reassurance that memory bias, if any, was nil.

With respect to bias conclusions, all bias favors the Comparator drug (original formula Viroxyn®) over the Treatment drug (Viroxyn® Professional with benzocaine). Both drugs are labeled to treat cold sores, and both have the same anti-viral ingredient at identical concentrations. Thus, for Viroxyn® Professional with benzocaine to show superiority to the Comparator drug (original formula Viroxyn®) in clinically relevant endpoints is indeed remarkable since the expected effect of the benzocaine is limited to an anesthetic action of extremely short duration and was intended to relieve user discomfort during application. For this outcome to be observed despite identified bias favoring original formula Viroxyn® makes the outcome for Viroxyn® Professional with benzocaine all the more dramatic and credible.

With respect to time to healing metric, even though all bias favored the Comparator cohort (original formula Viroxyn®), the Treatment cohort (Viroxyn® Professional) demonstrated dramatic and clinically relevant differences in time-to-healing when compared to original formula Viroxyn® (p=0.02) and Control (p<0.01) cohorts. As expected, original formula Viroxyn® also demonstrated an advantage in time-to-healing versus Control (p<0.01).

With respect to time to loss of discomfort metric, even though all bias favored the Comparator (Viroxyn®) cohort, the Treatment cohort (Viroxyn® Professional with benzocaine) demonstrated statistically significant and clinically relevant differences in time to persistent loss of pain versus Comparator (p=0.05) and Control (p<0.01). As expected, Comparator (original formula Viroxyn®) also demonstrated an advantage in time to loss of discomfort versus Control. (p<0.01).

In summary, while both drugs demonstrated clinically relevant advantages versus the untreated cold sores that served as the Control, the advantage clearly favors Treatment (Viroxyn® Professional with benzocaine) versus Comparator (original formula Viroxyn®). The fact that all identified biases favored Comparator adds credibility to the study outcome. Further credibility is suggested in that the Control value compares favorably with placebo outcome values published in other cold sore studies. The study conclusions strongly suggest that, given that both drugs have the same anti-viral active ingredient (benzalkonium chloride) and that the anti-viral ingredient is present in the same concentration (0.13%) in both drugs, a previously unexpected increase in overall efficacy has been created by the addition of the benzocaine that goes well beyond what a person skilled in the study of herpes labialis, would reasonably expect. The anesthetic effect of benzocaine is fast acting, but very short lived, and would not alone explain the observed results.

COMPARATIVE EXAMPLES

The following comparative examples are provided in order to compare how well compositions that do not contain benzocaine do that penetrate disordered tissue as well and therefore require rigorous agitation in order to promote good penetration into the disordered tissue.

Comparative Example 1

A cold sore treatment composition sold through dentists under the name Viroxin® has the following composition:

| | |
|---|---|
| Benzalkonium Chloride | 0.13% by weight |
| Liquid Carrier (IPA + H2O) | 99.87% by weight |
| Isopropyl Alcohol 70% v/v | |
| Water 30% v/v | |

This treatment composition was shown to work well in treating cold sores using an applicator such as the one illustrated in FIGS. 2A-2F together with applying the composition to the cold sore area using an applicator with vigorous rubbing to promote penetration of the composition into the cold sore. In many cases, the cold sore was so painful that users could not simply apply the composition all at once but often applied a first amount, which caused initial pain, and then a second amount once the pain was reduced to an acceptable level. The main impediment to effective treatment was lack of compliance by the user as a result of the intense pain caused by the composition combined with vigorous rubbing.

Comparative Example 2

The treatment composition of Comparative Example 1 was applied but only with slight rubbing. Soap was used on the cold sore treatment site that evening. Although the cold sore formed a scab after about two days, a new cold sore erupted at that time above the existing scab and spread itself into the scab.

WORKING EXAMPLES

In an attempt to ameliorate the pain associated with the treatment composition of Example 1, particularly when applied to an open sore, various amounts of benzocaine were added in an attempt to ensure better compliance by the user. Unexpectedly, benzocaine not only reduced the pain associated with application of the treatment composition, it also significantly enhanced penetration of the treatment composition beyond the amount of penetration of the composition in the absence of the benzocaine. This was demonstrated by the fact that effective treatment of cold sores was obtained with less rubbing and damage to the cold sore.

In the previous patents by the inventor, it was explicitly taught that vigorous rubbing, even to the point of causing tissue damage, was desirable and necessary in order for the treatment composition of Example 1 to properly penetrate into the cold sore and provide the desired killing of the cold sore viruses and neutralization of toxins released by the viruses.

In contrast, including benzocaine together with the other components significantly decreased the amount of rubbing that was required by the user in order to feel the sensation of penetration by the treatment composition down the nerves. Numbing can only occur when the composition penetrates deeply enough to reach the nerves. Such numbing was often felt simply by applying the composition with little or no rubbing, which objectively demonstrated that treatment compositions augmented with benzocaine have enhanced tissue penetration properties. While numbing of the cold sore site substantially decreased the pain and discomfort associated with application of the treatment composition and lessened the fear and reticence associated with rubbing the cold sore with the applicator (i.e., the same applicator used to apply the treatment composition of Example 1), it was surprisingly and unexpectedly found that significantly less, or even no, rubbing was typically required to obtain the same level of treatment as compared to treating cold sores with the composition of Example 1.

Following are various treatment compositions that were prepared, which are modifications of the composition of Example 1.

Example 3

| | |
|---|---|
| Benzocaine | 5% by weight |
| Benzalkonium Chloride | 0.13% by weight |
| Liquid Carrier (IPA + H2O) | 94.87% by weight |
| Isopropyl Alcohol 70% v/v | |
| Water 30% v/v | |

The composition of this Example provided enhanced penetration of cold sores as described herein and resulted in effective treatment of the cold sores with significantly less rubbing and pain compared to the composition of Example 1. In fact, effective treatment of cold sores occurred in many cases with little or no rubbing, or only very gentle rubbing. Numbing typically occurred within a few seconds (e.g., 2-5 seconds) and persisted for a few minutes (e.g., 2-5 minutes) and then subsided and restored use of the person's mouth. Such enhanced penetration compared to the composition of Example 1 was even more unexpected considering the fact that Example 3 included only 94.87% by weight of tissue penetrating liquid carrier while Example 1 included 99.87%.

While penetration into the cold sore was enhanced, there was, in a small number of cases, a slight amount of white benzocaine residue on the cold sore depending on the amount of treatment composition applied to the cold sore. It is postulated that, once the cold sore was fully saturated with the treatment composition, further penetration of the composition was inhibited. Because benzocaine is not volatile like the liquid carrier, it could not evaporate away and therefore remained on the surface. In most cases, however, no benzocaine residue was reported.

Example 4

| | |
|---|---|
| Benzocaine | 2.5% by weight |
| Benzalkonium Chloride | 0.13% by weight |
| Liquid Carrier (IPA + H2O) | 97.37% by weight |
| Isopropyl Alcohol 70% v/v | |
| Water 30% v/v | |

The composition of this Example provided enhanced penetration of cold sores as described herein and resulted in effective treatment of the cold sores with significantly less rubbing and pain compared to the composition of Example 1.

Effective treatment of cold sores occurred in many cases with little or no rubbing, or very gentle rubbing. The treatment composition of this Example enhanced penetration virtually the same degree as the composition of Example 3 and also resulted in initial numbing in a few seconds and subsidence of numbing after a few minutes but did not leave behind any residue.

The fact that the composition of Example 4 worked about as well as the composition of Example 3 is a surprising and unexpected result in view of the FDA Cold Sore Analgesic Monograph that requires a composition to include 5-20% benzocaine to be considered safe and effective. Including 2.5% by weight benzocaine was found to be virtually as effective as including 5% in reducing the sensation of pain.

Example 5

| | |
|---|---|
| Benzocaine | 10% by weight |
| Benzalkonium Chloride | 0.13% by weight |
| Liquid Carrier (IPA + H2O) | 89.87% by weight |
| Isopropyl Alcohol 70% v/v | |
| Water 30% v/v | |

The composition of this Example provided enhanced penetration of cold sores as described herein and resulted in effective treatment of the cold sores with significantly less rubbing and pain compared to the composition of Example 1. The treatment composition of this Example caused initial numbing within a few seconds but numbing persisted longer than in Examples 3 and 4. In addition, the composition left behind a significant amount of white benzocaine residue. Nevertheless, the treatment composition of this Example was superior to the composition of Example 1 in terms of patient compliance and efficacy.

Example 6

| | |
|---|---|
| Benzocaine | 20% by weight |
| Benzalkonium Chloride | 0.13% by weight |
| Liquid Carrier (IPA + H2O) | 79.87% by weight |
| Isopropyl Alcohol 70% v/v | |
| Water 30% v/v | |

The composition of this Example provided enhanced penetration of cold sores as described herein and resulted in effective treatment of the cold sores with significantly less rubbing and pain compared to the composition of Example 1. The treatment composition of this Example caused initial numbing within a few seconds but numbing persisted for over 1 hour in many cases, which many patients found objectionable due to the loss of normal use of their lips and mouth. In addition, the composition left behind an even greater amount of white benzocaine residue than in Example 5. Nevertheless, the treatment composition of this Example was superior to the composition of Example 1 in terms of patient compliance and efficacy.

Example 7

| | |
|---|---|
| Benzocaine | 1.25% by weight |
| Benzalkonium Chloride | 0.13% by weight |
| Liquid Carrier (IPA + H2O) | 98.62% by weight |
| Isopropyl Alcohol 70% v/v | |
| Water 30% v/v | |

The composition of this Example provided effective treatment of the cold sores but did not penetrate as rapidly and did not numb the pain as quickly or as completely as when larger amounts of benzocaine were included. In the case of cold sores that were not open, the composition of this Example could not completely numb the disordered tissue.

HYPOTHETICAL EXAMPLES

The following are hypothetical and are given by way of example in order to show other compositions within the scope of the invention and how they would be expected to perform based on test data obtained relative to working Examples 3-7 and Comparative Examples 1-2.

Example 8

| | |
|---|---|
| Benzocaine | 4% by weight |
| Benzalkonium Chloride | 0.13% by weight |
| Liquid Carrier (IPA + H2O) | 95.87% by weight |
| Isopropyl Alcohol 70% v/v | |
| Water 30% v/v | |

The composition of this Example provides enhanced penetration of cold sores as described herein and results in effective treatment of the cold sores with significantly less rubbing and pain compared to the composition of Example 1. The treatment composition of this Example enhances penetration virtually the same degree as the composition of Example 3 but does not leave behind any significant or noticeable benzocaine residue.

Example 9

| | |
|---|---|
| Benzocaine | 3% by weight |
| Benzalkonium Chloride | 0.13% by weight |
| Liquid Carrier (IPA + H2O) | 96.87% by weight |
| Isopropyl Alcohol 70% v/v | |
| Water 30% v/v | |

The composition of this Example provides enhanced penetration of cold sores as described herein and results in effective treatment of the cold sores with significantly less rubbing and pain compared to the composition of Example 1. The treatment composition of this Example enhances penetration virtually the same as the composition that included 2.5% benzocaine. It is possible that this composition is able to numb disordered tissue slightly faster and/or more completely than when 2.5% benzocaine is used.

Example 10

| | |
|---|---|
| Benzocaine | 2% by weight |
| Benzalkonium Chloride | 0.13% by weight |
| Liquid Carrier (IPA + H2O) | 97.87% by weight |
| Isopropyl Alcohol 70% v/v | |
| Water 30% v/v | |

The composition of this Example provides enhanced penetration of cold sores as described herein and results in effective treatment of the cold sores with somewhat less rubbing and pain compared to the composition of Example 1. The treatment composition of this Example enhances penetration and does not leave behind any benzocaine residue but does not work quite as well at rapidly reducing pain as compared to when larger amounts of benzocaine are used. The penetration enhancing effect of benzocaine is less than when greater amounts of benzocaine are used. Accordingly, when using a liquid carrier consisting of 70% by volume isopropyl alcohol in water, including more than 2% benzocaine is more effective in reducing pain and enhancing penetration when treating cold sores or other disordered tissue.

Example 11

| | |
|---|---|
| Benzocaine | 6% by weight |
| Benzalkonium Chloride | 0.13% by weight |
| Liquid Carrier (IPA + H2O) | 93.87% by weight |
| Isopropyl Alcohol 70% v/v | |
| Water 30% v/v | |

The composition of this Example provides enhanced penetration of cold sores as described herein and results in effective treatment of the cold sores with significantly less rubbing and pain compared to the composition of Example 1. Penetration is enhanced about the same as when 5% benzocaine is used but there is slightly more benzocaine residue depending on the amount of treatment composition applied to the cold sore. As discussed above, it is possible that once a cold sore is fully saturated with the treatment composition, further penetration of the composition is inhibited. Because benzocaine is not volatile like the liquid carrier, it cannot evaporate away and can leave a residue once the cold sore becomes saturated and further penetration is inhibited.

Example 12

| | |
|---|---|
| Benzocaine | 7.5% by weight |
| Benzalkonium Chloride | 0.13% by weight |
| Liquid Carrier (IPA + H2O) | 92.37% by weight |
| Isopropyl Alcohol 70% v/v | |
| Water 30% v/v | |

The composition of this Example provides enhanced penetration of cold sores as described herein and results in effective treatment of the cold sores with significantly less rubbing and pain compared to the composition of Example 1. Penetration is enhanced as when 5% benzocaine is used but there is more benzocaine residue depending on the amount of treatment composition applied to the cold sore.

Example 13

| | |
|---|---|
| Benzocaine | 15% by weight |
| Benzalkonium Chloride | 0.13% by weight |
| Liquid Carrier (IPA + H2O) | 84.87% by weight |
| Isopropyl Alcohol 70% v/v | |
| Water 30% v/v | |

The composition of this Example provides enhanced penetration of cold sores as described herein and results in effective treatment of the cold sores with significantly less rubbing and pain compared to the composition of Example 1. Penetration is enhanced as when smaller quantities of benzocaine are used but there is substantially more benzocaine residue depending on the amount of treatment composition applied to the cold sore. In addition, the disordered tissue remains numb for a longer amount of time than when smaller quantities of benzocaine are used.

Example 14

Any of the foregoing examples is modified by substituting the identified liquid carrier with a liquid carrier comprised of 80%, 90% or 100% by volume isopropyl alcohol and/or an organic solvent that is more penetrating than isopropyl alcohol. The treatment compositions have even further enhanced penetration and can provide adequate penetration into cold sores or other disordered tissue using the same or smaller quantities of benzocaine.

Example 15

Any of the foregoing examples is modified by substituting the liquid carrier with a liquid carrier comprised of 60%, 50%, 40%, 30% or 20% by volume isopropyl alcohol and/or an organic solvent that is less penetrating than isopropyl alcohol. The treatment compositions provide enhanced penetration into cold sores or other disordered tissue compared to the same compositions in the absence of benzocaine but benefit from including larger quantities of benzocaine.

Example 16

Any of the foregoing examples is modified so that the amount of benzalkonium chloride is included in an amount of 0.01%, 0.05%, 0.1%, 0.15%, 0.2%, 0.25%, 0.3%, 0.4% or 0.5% by weight. The treatment compositions provide enhanced penetration into cold sores or other disordered tissue compared to the same compositions in the absence of benzocaine. Less composition is required to provide a desired treatment level and/or may benefit from using a less penetrating liquid system to offset the greater toxicity when including more than 0.13% benzalkonium chloride. Conversely, more composition is required to provide a desired treatment level and/or may benefit from using a more penetrating liquid system when including less than 0.13% benzalkonium chloride.

Example 17

Any of the foregoing examples is modified by combining or substituting benzalkonium chloride with one or more of the following organohalides: benzethonium chloride, methyl benzethonium chloride, cetyl pyridinium chloride, chloroxylenol, hexachlorophene, triclosan, or chlorhexidine. Depending on the level of toxicity or anti-pathogenic activity of a given organohalide, it may be beneficial adjust the concentration of anti-infective agent to provide a desired level of anti-infective activity in view of the penetrating qualities of the overall treatment composition. The treatment compositions are useful in treating a wide variety of disordered tissues caused by viruses, bacteria, fungi or non-pathogenic toxins.

Example 18

Any of the foregoing examples is modified by combining or substituting benzalkonium chloride with one or more of the following organohalides: quaternary ammonium halide having an alkyl group with 6-18 carbons including mixtures of varied alkyl chains, ethoxylated quaternary ammonium halides including mixtures of alkyl chains, alkyl benzyl dimethyl ammonium halide, alkyl dimethyl ethyl benzyl ammonium halide, n-alkyl dimethyl benzyl ammonium halide, diisobutyl phenoxy ethoxy ethyl dimethyl benzyl ammonium halide, n-($C_{12}C_{14}C_{16}$) alkyl dimethyl benzyl ammonium halide, dodecyl dimethyl ammonium halide, dioctyl dimethyl ammonium halide, dialkyl dimethyl ammonium halide, dialkyl methyl benzyl ammonium halide, octyl decyl dimethyl ammonium halide, lauryl dimethyl benzyl ammonium halide, o-benzyl-p-chlorophenol, dideryl dimethyl ammonium halide, dioctyl dimethyl ammonium halide, or alkyl ($C_{14}C_{12}C_{16}$) dimethyl benzyl ammonium halide. Depending on the level of toxicity or anti-pathogenic activity of a given organohalide, it may be beneficial adjust the concentration of anti-infective agent to provide a desired level of anti-infective activity in view of the penetrating qualities of the overall treatment composition. The treatment compositions are useful in treating a wide variety of disordered tissues caused by viruses, bacteria, fungi or non-pathogenic toxins.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed is:

1. A method for the treatment of disordered tissue caused by a herpes virus by administering a treatment composition in a subject in need thereof comprising:
at least one benzalkonium chloride compound

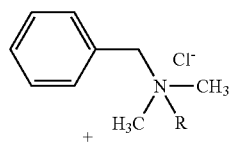

where R=$X_8H_{17}$ to $C_{18}H_{37}$;
a liquid carrier comprising a tissue penetrating component for penetrating disordered tissue in a rapid manner without rapidly diffusing beyond the skin; and
benzocaine present in an amount ranging from 3.5% to about 20% so that the treatment composition is more effective in treating disordered tissue caused by a herpes virus compared to the treatment composition in the absence of benzocaine.

2. the method of treatment as recited in claim 1, wherein the at least one benzalkonium chloride compound is included in a concentration in a range from about 0.01% to about 0.5% by weight of the treatment composition.

3. A method of treatment as recited in claim 1, wherein the at least one benzalkonium chloride compound is included in a concentration in a range from about 0.05% to about 0.3% by weight of the treatment composition.

4. A method of treatment as recited in claim 1, wherein the at least one benzalkonium chloride compound is included in a concentration in a range from about 0.1% to about 0.2% by weight of the treatment composition.

5. The method of treatment as recited in claim 1, wherein the benzocaine increases residence time of the benzalkonium chloride compound in a treatment area by at least about 10% compared to the treatment composition in the absence of the benzocaine.

6. The method of treatment as recited in claim 1, wherein the benzocaine increases residence time of the benzalkonium chloride compound in a treatment area by about 20% to about 100% compared to the treatment composition in the absence of the benzocaine.

7. The method of treatment as recited in claim 1, wherein the liquid carrier comprises isopropyl alcohol and water, the isopropyl alcohol comprising from about 50% to about 80% by volume of the liquid carrier.

8. The method of treatment as recited in claim 1, wherein the liquid carrier is less penetrating than a liquid carrier consisting of 50% by volume isopropyl alcohol and 50% by volume water.

9. The method of treatment as recited in claim 8, wherein the benzocaine is included in a range of about 4% to about 15% by weight of the treatment composition.

10. The method of treatment as recited in claim 8, wherein the benzocaine is included in a range of about 4.5% to about 10% by weight of the treatment composition.

11. The method of treatment as recited in claim 1, wherein the benzocaine is included in a range of about 5% to about 7.5% by weight of the treatment composition.

12. The method of treatment as recited in claim 1, wherein the liquid carrier is more penetrating than a liquid carrier consisting of 80% by volume isopropyl alcohol and 20% by volume water.

13. The method of treatment as recited in claim 1, wherein the treatment composition is void of penetration inhibiting oils.

14. A method for the treatment of disordered tissue caused by a herpes virus by administering a treatment composition in a subject in need thereof comprising:
at least one anti-infective agent in a tissue penetrating liquid carrier, the benzalkonium chloride compound:

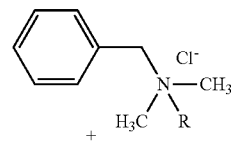

where R=$C_8H_{17}$ to $C_{18}H^{37}$; and the tissue penetrating liquid carrier comprising isopropyl alcohol and water, the isopropyl alcohol comprising from about 50% to about 80% by volume of the liquid carrier; and
benzocaine present in an amount ranging from 3.5% to about 20% by weight of the treatment composition so that the treatment composition is more effective in treating disordered tissue caused by a herpes virus compared to the treatment composition in the absence of benzocaine.

15. A method for the treatment of disordered tissue caused by a herpes virus by administering a treatment composition in a subject in need thereof comprising:
at least one benzalkonium chloride compound:

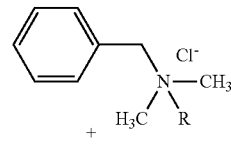

where R=$C_8H_{17}$ to $C_{18}H_{37}$; and the liquid carrier comprising a tissue penetrating component for penetrating disordered tissue in a rapid manner without rapidly diffusing beyond the skin, wherein the liquid carrier is less penetrating than a liquid carrier consisting of 50% by volume isopropyl alcohol and 50% by volume water; and benzocaine present in an amount ranging from 3.5% to about 20% by weight of the treatment composition so that the treatment composition is more effective in treating disordered tissue caused by a herpes virus compared to the treatment composition in the absence of the benzocaine.

16. The method of treatment as recited in claim 15, wherein the benzocaine is included in a concentration in a range of about 4% to about 15% by weight of the treatment composition.

17. The method of treatment as recited in claim 15, wherein the benzocaine is included in a concentration in a range of about 4.5% to about 10% by weight of the treatment composition.

18. The method of treatment as recited in claim 15, wherein the benzocaine is included in a range of about 5% to about 7.5% by weight of the treatment composition.

\* \* \* \* \*